US008878749B1

(12) United States Patent
Wu et al.

(10) Patent No.: US 8,878,749 B1
(45) Date of Patent: Nov. 4, 2014

(54) SYSTEMS AND METHODS FOR POSITION ESTIMATION

(75) Inventors: Bo Wu, Alhambra, CA (US); Yong Zhao, San Jose, CA (US); Thad Eugene Starner, Mountain View, CA (US); Hayes Solos Raffle, Palo Alto, CA (US)

(73) Assignee: Google Inc., Mountain View, CA (US)

( * ) Notice: Subject to any disclaimer, the term of this patent is extended or adjusted under 35 U.S.C. 154(b) by 211 days.

(21) Appl. No.: 13/620,904

(22) Filed: Sep. 15, 2012

Related U.S. Application Data

(60) Provisional application No. 61/584,139, filed on Jan. 6, 2012.

(51) Int. Cl.
*G09G 5/00* (2006.01)

(52) U.S. Cl.
USPC ............... 345/8; 359/630; 351/209; 348/115

(58) Field of Classification Search
USPC .......... 345/8; 359/13, 630; 351/208, 209, 210
See application file for complete search history.

(56) References Cited

U.S. PATENT DOCUMENTS

| 7,773,111 B2 * | 8/2010 | Cleveland et al. | 348/135 |
| 7,997,730 B2 * | 8/2011 | Cleveland | 351/210 |

OTHER PUBLICATIONS

Perez et al., "A Precise Eye-Gaze Detection and Tracking System," WSCG 2003 (Union Agency—Science Press).
Hammoud, Passive Eye Monitoring, Algorithms, Applications and Experiments, Springer Series on Signals and Communication Technology, 2008, pp. 111-131, 135-141, 202-209.
R. Valenti and T. Gevers, Accurate Eye Center Location and Tracking Using Isophote Curvature (CVPR 2008).
Cerrolaza et al., Taxonomic Study of Polynomial Regressions Applied to the Calibration of Video-Oculographic Systems, ETRA '08 Proceedings of the 2008 Symposium on Eye Tracking Research and Applications.
Nagamatsu, Takashi et al., Gaze Estimation Method Based on an Aspherical Model of the Cornea: Surface of Revolution About the Optical Axis of the Eye, Association for Computing Machinery, Inc., 2010.
Yoo, Dong Hyun et al., Non-Intrusive Eye Gaze Estimation Without Knowledge of Eye Pose, Sixth IEEE International Conference on Automatic Face and Gesture Recognition, 2004.

* cited by examiner

*Primary Examiner* — Abbas Abdulselam
(74) *Attorney, Agent, or Firm* — McDonnell Boehnen Hulbert & Berghoff LLP

(57) ABSTRACT

Systems and methods are described for improving gaze estimation based on glints. An example method may be executable to receive glint-location data indicating a location for each of one or more glints that are reflected from an eye. The glint-location data may be captured by an imaging device that is attached to a head-mountable display (HMD). The method may be further executable to determine a plurality of normalized pupil locations comprising at least a first and a second normalized pupil location. Each normalized pupil location may be determined based on the glint-location data for a different combinatoric subset of the one or more glints. The method may be further executable to determine a regression model to fit the plurality of normalized pupil locations to an expected gaze location, and perform a gaze-tracking process based on the regression model.

20 Claims, 16 Drawing Sheets

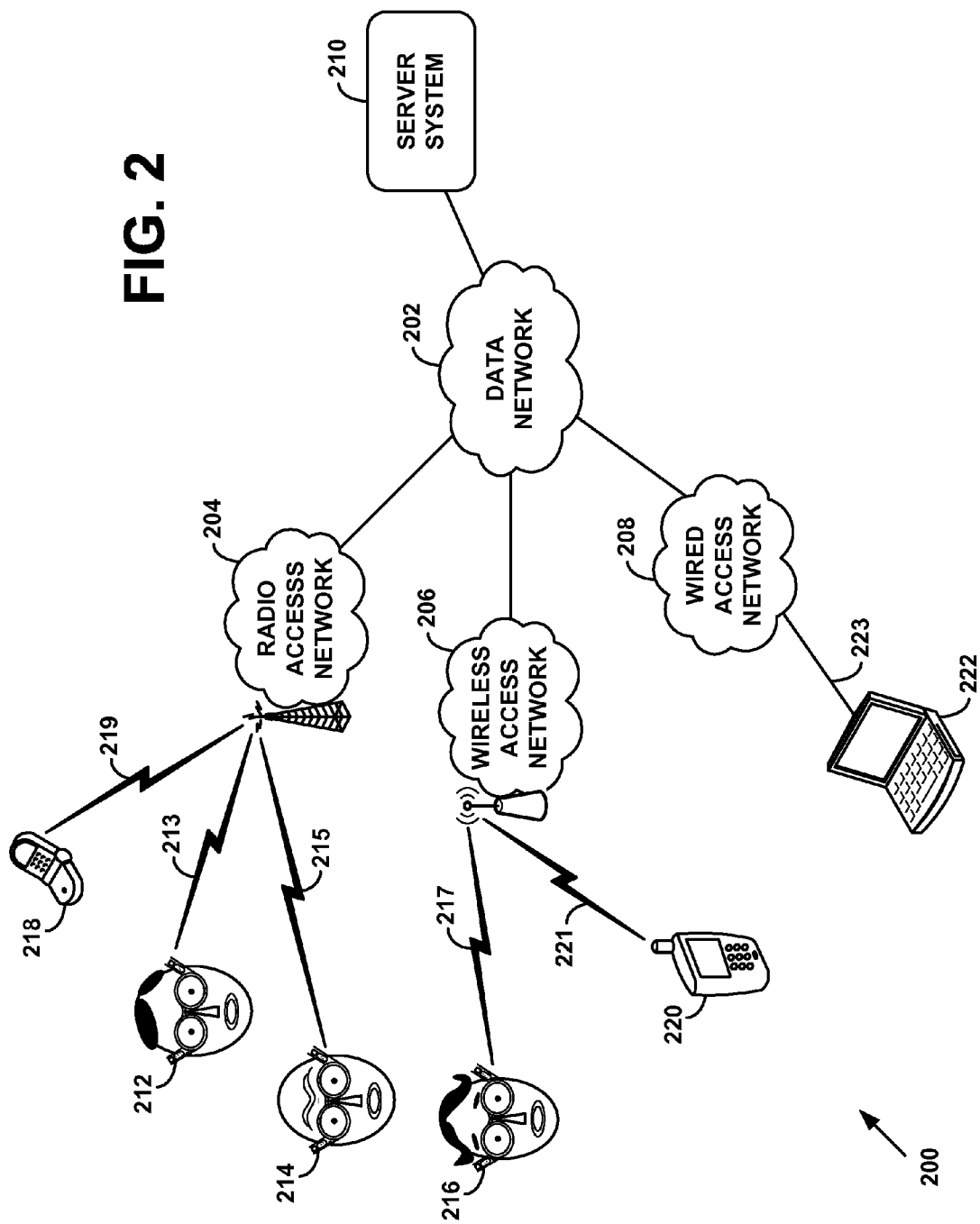

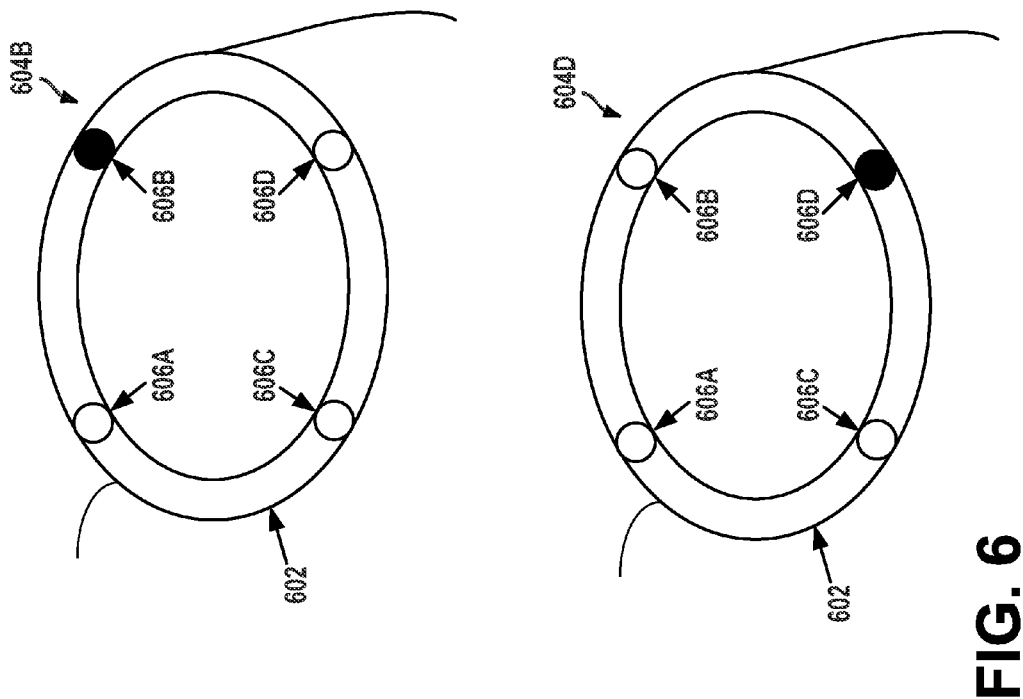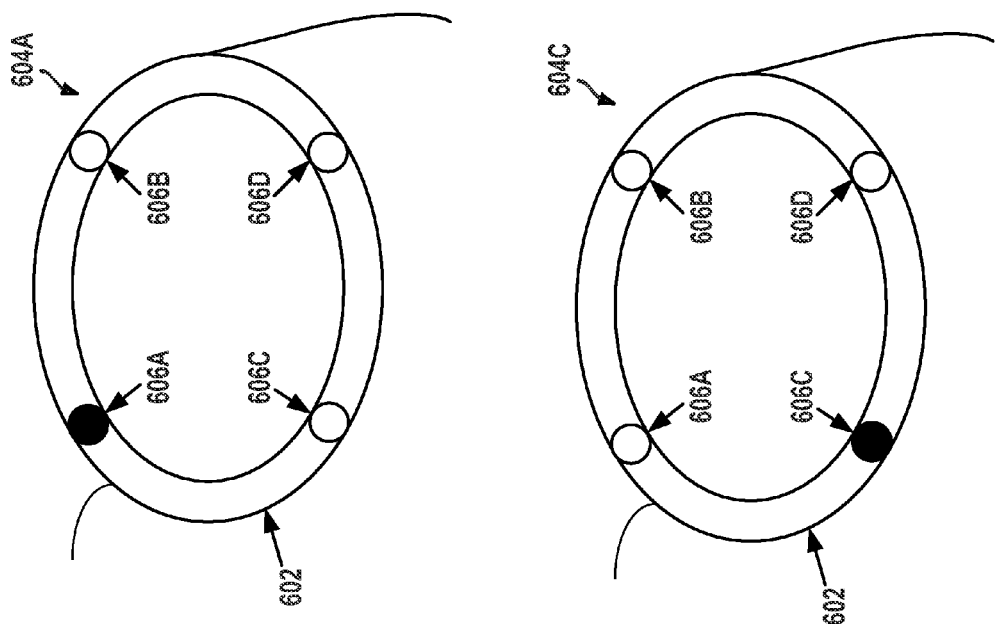
FIG. 6

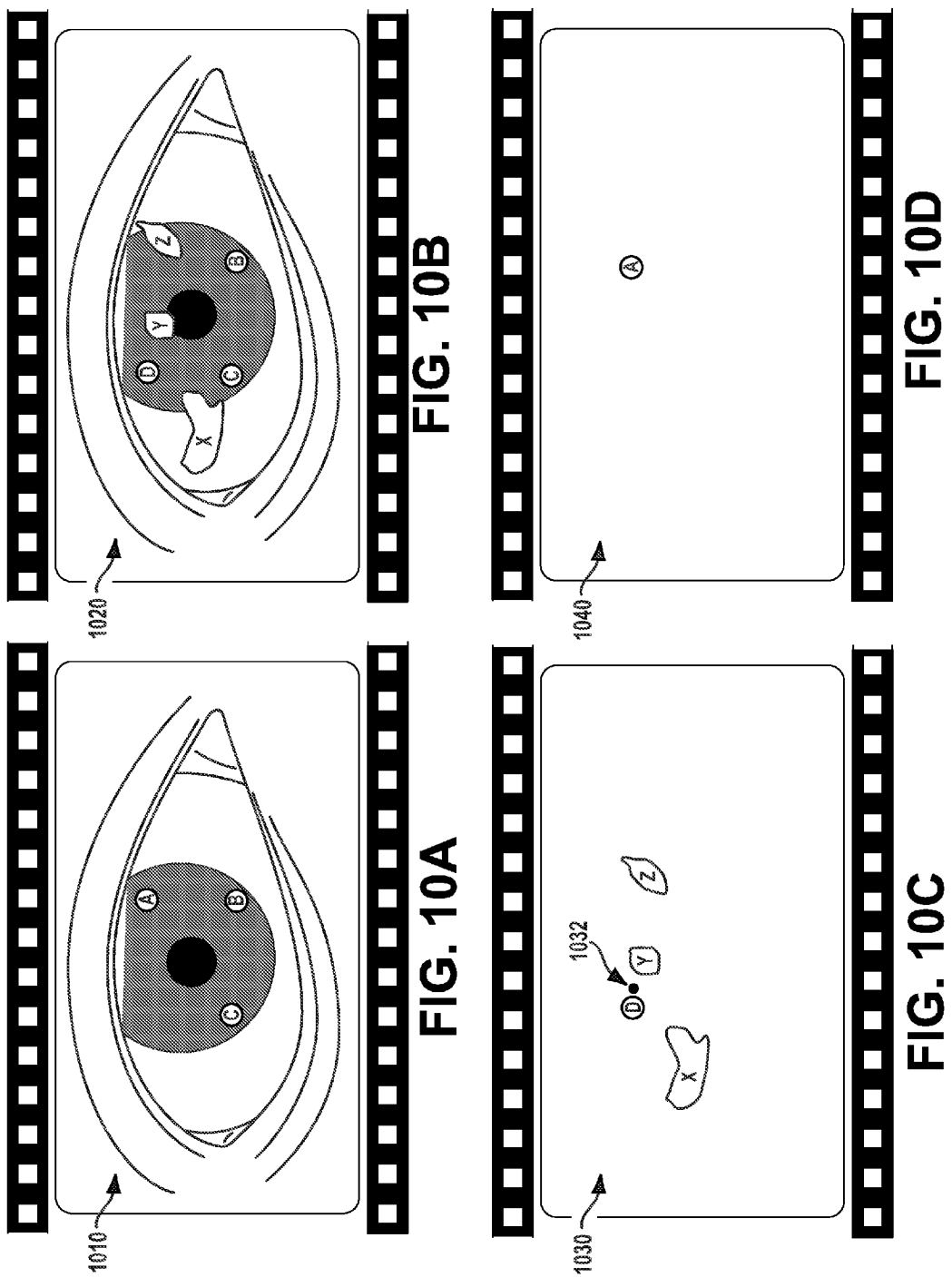

SYSTEMS AND METHODS FOR POSITION ESTIMATION

CROSS-REFERENCE TO RELATED APPLICATIONS

This patent application claims priority to U.S. Application No. 61/584,139, filed Jan. 6, 2012, the contents of which are entirely incorporated herein by reference, as if fully set forth in this application.

BACKGROUND

Unless otherwise indicated herein, the materials described in this section are not prior art to the claims in this application and are not admitted to be prior art by inclusion in this section.

Computing devices such as personal computers, laptop computers, tablet computers, cellular phones, and countless types of Internet-capable devices are increasingly prevalent in numerous aspects of modern life. Over time, the manner in which these devices are providing information to users is becoming more intelligent, more efficient, more intuitive, and/or less obtrusive.

The trend toward miniaturization of computing hardware, peripherals, as well as of sensors, detectors, and image and audio processors, among other technologies, has helped open up a field sometimes referred to as "wearable computing." In the area of image and visual processing and production, in particular, it has become possible to consider wearable displays that place a very small image display element close enough to a wearer's (or user's) eye(s) such that the displayed image fills or nearly fills the field of view, and appears as a normal sized image, such as might be displayed on a traditional image display device. The relevant technology may be referred to as "near-eye displays."

Near-eye displays are fundamental components of wearable displays, also sometimes called "head-mounted displays" (HMDs). A head-mounted display places a graphic display or displays close to one or both eyes of a wearer. To generate the images on a display, a computer processing system may be used. Such displays may occupy a wearer's entire field of view, or only occupy part of the wearer's field of view. Further, head-mounted displays may be as small as a pair of glasses or as large as a helmet.

Emerging and anticipated uses of wearable displays include applications in which users interact in real time with an augmented or virtual reality. Such applications can be mission-critical or safety-critical, such as in a public safety or aviation setting. The applications can also be recreational, such as interactive gaming.

SUMMARY

In one aspect, an example method may be executable to receive glint-location data indicating a location for each of one or more glints that are reflected from an eye and determine a plurality of normalized pupil locations. The glint-location data may be captured by an imaging device that is associated with a head-mountable display (HMD). The plurality of normalized pupil locations may include at least a first and a second normalized pupil location. Each normalized pupil location may be determined based on the glint-location data for a different combinatoric subset of the one or more glints. The method may be further executable to determine a regression model to fit the plurality of normalized pupil locations to an expected gaze location and to perform, by a computing device, a gaze-tracking process based on the regression model.

In another aspect, an example computing device can include a processor, a voice interface, a non-transitory computer-readable medium and/or program instructions stored on the non-transitory computer-readable medium. The program instructions may be executable by the processor to cause the wearable computing device to perform one or more functions. The functions may include: receiving glint-location data indicating a location for each of one or more glints that are reflected from an eye, wherein the glint-location data may be captured by an imaging device that is associated with an HMD; determining a plurality of normalized pupil locations comprising at least a first and a second normalized pupil location, where each normalized pupil location is determined based on the glint-location data for a different combinatoric subset of the one or more glints; determining a regression model to fit the plurality of normalized pupil locations to an expected gaze location; and performing a gaze-tracking process based on the regression model.

In yet another aspect, an article of manufacture can include a non-transitory computer-readable medium having instructions stored thereon that, when executed by a computing device, may cause the computing device to perform any number of functions. The functions may include: receiving glint-location data indicating a location for each of one or more glints that are reflected from an eye, wherein the glint-location data may be captured by an imaging device that is associated with an HMD; determining a plurality of normalized pupil locations comprising at least a first and a second normalized pupil location, where each normalized pupil location is determined based on the glint-location data for a different combinatoric subset of the one or more glints; determining a regression model to fit the plurality of normalized pupil locations to an expected gaze location; and performing, by a computing device, a gaze-tracking process based on the regression model.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2 is a simplified illustration of a network via which one or more devices may engage in communications, according to an exemplary embodiment;

FIG. 6 is a simplified illustration of a predetermined sequence of light-source combinations, according to an exemplary embodiment;

FIGS. 10A and 10B illustrate a first frame and a second frame of infrared image data, respectively, according to an illustrative scenario;

FIGS. 10C and 10D are simplified illustrations of frame differences, according to an illustrative embodiment;

DETAILED DESCRIPTION

Figure 1A:
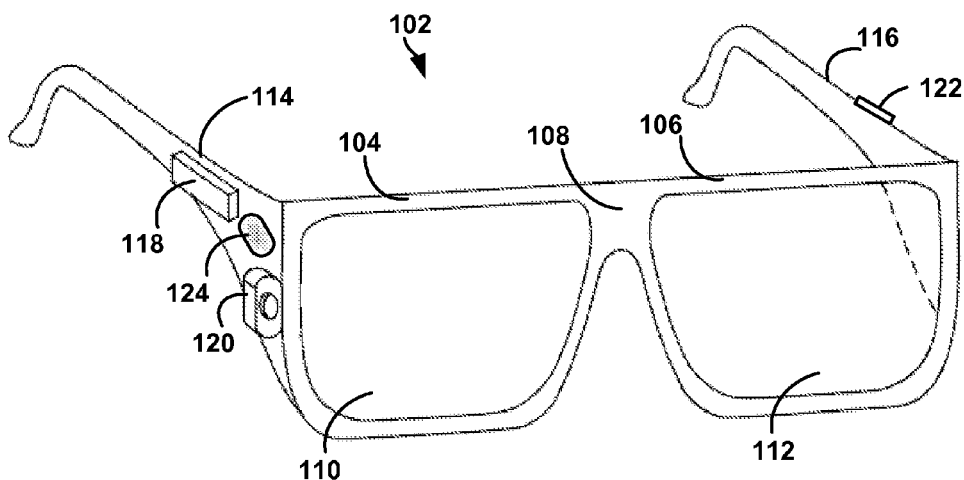
FIG. 1A illustrates a wearable computing system according to an exemplary embodiment.

Exemplary methods and systems are described herein. It should be understood that the word "exemplary" is used herein to mean "serving as an example, instance, or illustration." Any embodiment or feature described herein as "exemplary" is not necessarily construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

I. OVERVIEW

Some eye-tracking techniques utilize "controlled glints" to determine eye movements. In particular, a number of light sources may be directed at the eye such that the reflections of these light sources in the eye (i.e., the controlled glints) may be captured and/or recorded by an imaging device, such as a video camera or a series of single pixel detectors, that may also be directed at the eye or distinct regions of the eye. The controlled glints may then be analyzed to determine the general position of the eye.

As a specific example, four light sources may be configured to provide a square or rectangular arrangement of glints on the eye. However, due to the shape of the eye, the generally square arrangement of glints will be warped according to the position of the eye. Accordingly, the manner in which the arrangement of glints warps from frame to frame may be analyzed to determine how the eye has moved between frames.

More specifically, to determine eye movement from controlled glints, frames of the video image may be flattened. The flattening process maps the ellipsoid shape of the corneal surface of the eye to a two-dimensional image, such that the actual distance between glints on the corneal surface is represented in the two-dimensional image. An exemplary system may then determine optical flow between the flattened frames, which is indicative of how the glints moved between frames. The optical flow may then be re-mapped to the corneal surface in order to determine how the eye has moved.

Further, in some embodiments, the above described flattening process and/or optical flow analysis may not by utilized. Instead, an exemplary embodiment may employ a calibration process in which a number of targets are sequentially displayed to the wearer of an HMD. As the wearer looks at the targets, an exemplary system may capture images of the eye. Knowing that the wearer will look in a certain direction in order to look at each target, the system may determine the respective pattern of glints in the image or images that correspond to the display of each target. The position of the eye corresponding to the display of each target may therefore be associated with the pattern of glints in the corresponding image or images of the eye. Further, the system may interpolate between the glint patterns for known eye positions to determine glint patterns for other eye positions.

In fact, by using such a technique, an exemplary system might track the position of the eye by learning the relationship between the pattern of glints in an image of the eye and the position of the pupil (e.g., determining a mapping between the glint pattern and eye position), without necessarily relying on complex geometry. Details of such an approach, albeit applied to dark pupil tracking, are described in Perez et al., "A Precise Eye-Gaze Detection and Tracking System," WSCG 2003 (UNION Agency—Science Press).

While analysis of controlled glints may be an efficient technique for eye-tracking in some scenarios, ambient light can often interfere with controlled glints. More specifically, ambient light may also reflect of the eye and create "ambient glints," which may also be captured by the video of the eye. In some instances, the ambient-light reflections may make it difficult or even impossible to determine whether a glint is a controlled glint or an ambient glint. Thus, ambient light can make eye-tracking data based on controlled glints inaccurate.

In order to help distinguish controlled glints from ambient glints, an exemplary embodiment may switch off one light source in each frame, and rotate the light source that is switched off. For example, consider the above example with four light sources configured to provide a generally square arrangement of controlled glints. In this configuration, an exemplary system may switch off one light source during each frame of the video, rotating the switched-off light source such that each light source is switched off every fourth frame. As such, the general structure of the controlled glints will be known in each frame, which may help to distinguish the controlled glints from ambient glints.

In a further aspect of an exemplary embodiment, the light sources and the video camera to capture the glints may be implemented on a wearable computer with a head-mounted display (HMD). In particular, the lens frame of a glasses-style HMD may include an array of inward-facing light sources (e.g., LEDs) and an inward-facing video camera, which are both directed at the eye.

II. EXEMPLARY SYSTEMS

A. Exemplary Wearable Computing Devices

Systems and devices in which exemplary embodiments may be implemented will now be described in greater detail. In general, an exemplary system may be implemented in or may take the form of a wearable computer. In particular, an exemplary system may be implemented in association with or take the form of a head-mountable display (HMD), or a computing system that receives data from an HMD, such as a cloud-based server system.

However, an exemplary system may also be implemented in or take the form of other devices, such as a mobile phone, among others. Further, an exemplary system may take the form of non-transitory computer readable medium, which has program instructions stored thereon that are executable by at least one processor to provide the functionality described herein. An exemplary system may also take the form of a device such as a wearable computer or mobile phone, or a subsystem of such a device, which includes such a non-transitory computer readable medium having such program instructions stored thereon.

FIG. 1A illustrates a wearable computing system according to an exemplary embodiment. In FIG. 1A, the wearable computing system takes the form of a head-mounted device (HMD) 102 (which may also be referred to as a head-mounted display). It should be understood, however, that exemplary systems and devices may take the form of or be implemented within or in association with other types of devices, without departing from the scope of the invention. As illustrated in FIG. 1A, the head-mounted device 102 comprises frame elements including lens-frames 104, 106 and a center frame support 108, lens elements 110, 112, and extending side-arms 114, 116. The center frame support 108 and the extending side-arms 114, 116 are configured to secure the head-mounted device 102 to a user's face via a user's nose and ears, respectively.

Each of the frame elements 104, 106, and 108 and the extending side-arms 114, 116 may be formed of a solid structure of plastic and/or metal, or may be formed of a hollow structure of similar material so as to allow wiring and component interconnects to be internally routed through the head-mounted device 102. Other materials may be possible as well.

One or more of each of the lens elements 110, 112 may be formed of any material that can suitably display a projected image or graphic. Each of the lens elements 110, 112 may also be sufficiently transparent to allow a user to see through the lens element. Combining these two features of the lens elements may facilitate an augmented reality or heads-up display where the projected image or graphic is superimposed over a real-world view as perceived by the user through the lens elements.

The extending side-arms 114, 116 may each be projections that extend away from the lens-frames 104, 106, respectively, and may be positioned behind a user's ears to secure the head-mounted device 102 to the user. The extending side-arms 114, 116 may further secure the head-mounted device 102 to the user by extending around a rear portion of the user's head. Additionally or alternatively, for example, the HMD 102 may connect to or be affixed within a head-mounted helmet structure. Other possibilities exist as well.

The HMD 102 may also include an on-board computing system 118, a video camera 120, a sensor 122, and a finger-operable touch pad 124. The on-board computing system 118 is shown to be positioned on the extending side-arm 114 of the head-mounted device 102; however, the on-board computing system 118 may be provided on other parts of the head-mounted device 102 or may be positioned remote from the head-mounted device 102 (e.g., the on-board computing system 118 could be wire- or wirelessly-connected to the head-mounted device 102). The on-board computing system 118 may include a processor and memory, for example. The on-board computing system 118 may be configured to receive and analyze data from the video camera 120 and the finger-operable touch pad 124 (and possibly from other sensory devices, user interfaces, or both) and generate images for output by the lens elements 110 and 112.

The video camera 120 is shown positioned on the extending side-arm 114 of the head-mounted device 102; however, the video camera 120 may be provided on other parts of the head-mounted device 102. The video camera 120 may be configured to capture images at various resolutions or at different frame rates. Many video cameras with a small form-factor, such as those used in cell phones or webcams, for example, may be incorporated into an example of the HMD 102. While a video camera 120 is described herein, it should be understood that any number of imaging devices, such as a series of single pixel detectors, may be used to capture and/or record images. For example, functionality described herein may utilize images from a series of single pixel detectors that are arranged such that when an HMD is worn, each single-pixel detector is directed towards and captures image data from a different location on or near to the eye.

Further, although FIG. 1A illustrates one video camera 120, more video cameras may be used, and each may be configured to capture the same view, or to capture different views. For example, the video camera 120 may be forward facing to capture at least a portion of the real-world view perceived by the user. This forward facing image captured by the video camera 120 may then be used to generate an augmented reality where computer generated images appear to interact with the real-world view perceived by the user.

The sensor 122 is shown on the extending side-arm 116 of the head-mounted device 102; however, the sensor 122 may be positioned on other parts of the head-mounted device 102. The sensor 122 may include one or more of a gyroscope or an accelerometer, for example. Other sensing devices may be included within, or in addition to, the sensor 122 or other sensing functions may be performed by the sensor 122.

The finger-operable touch pad 124 is shown on the extending side-arm 114 of the head-mounted device 102. However, the finger-operable touch pad 124 may be positioned on other parts of the head-mounted device 102. Also, more than one finger-operable touch pad may be present on the head-mounted device 102. The finger-operable touch pad 124 may be used by a user to input commands. The finger-operable touch pad 124 may sense at least one of a position and a movement of a finger via capacitive sensing, resistance sensing, or a surface acoustic wave process, among other possibilities. The finger-operable touch pad 124 may be capable of sensing finger movement in a direction parallel or planar to the pad surface, in a direction normal to the pad surface, or both, and may also be capable of sensing a level of pressure applied to the pad surface. The finger-operable touch pad 124 may be formed of one or more translucent or transparent insulating layers and one or more translucent or transparent conducting layers. Edges of the finger-operable touch pad 124 may be formed to have a raised, indented, or roughened surface, so as to provide tactile feedback to a user when the user's finger reaches the edge, or other area, of the finger-operable touch pad 124. If more than one finger-operable touch pad is present, each finger-operable touch pad may be operated independently, and may provide a different function.

Figure 1B:
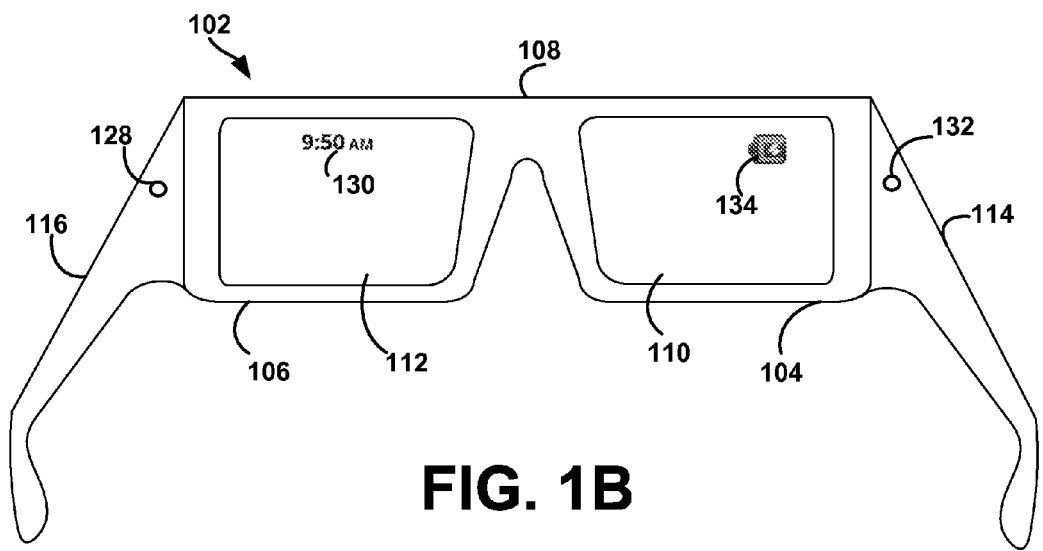
FIG. 1B illustrates an alternate view of the wearable computing device illustrated in FIG. 1A.

FIG. 1B illustrates an alternate view of the wearable computing device illustrated in FIG. 1A. As shown in FIG. 1B, the lens elements 110, 112 may act as display elements. The head-mounted device 102 may include a first projector 128 coupled to an inside surface of the extending side-arm 116 and configured to project a display 130 onto an inside surface of the lens element 112. Additionally or alternatively, a second projector 132 may be coupled to an inside surface of the extending side-arm 114 and configured to project a display 134 onto an inside surface of the lens element 110.

The lens elements 110, 112 may act as a combiner in a light projection system and may include a coating that reflects the light projected onto them from the projectors 128, 132. In some embodiments, a reflective coating may not be used (e.g., when the projectors 128, 132 are scanning laser devices).

Although not explicitly shown in the figures, the HMD could include an eye-tracking system or a portion of such a system. In an exemplary embodiment, the HMD could include inward- or rearward-facing (i.e., eye-facing) light source(s) and/or camera(s) to facilitate eye-tracking functions. For example, an HMD may include inward-facing light sources, such as an LED(s), at generally known location(s) with respect to one another and/or with respect to an eye under observation. The inward-facing camera may therefore capture images that include the reflections of the light source(s) off the eye; or in other words, images that capture the controlled glints that correspond to the inward-facing light sources. As such, the positioning of the controlled glints in a given image may be indicative of the position of the eye at the time the image was captured.

In a further aspect, with the above configuration, successive video frames may capture movement of the controlled in the image plane as the one or more eyes move. Thus, with the relative geometry of the controlled light source and the one or more eyes known, the observed movement of the controlled glints in the image plane may be analyzed in order to measure the movement of the eye.

In alternative embodiments, other types of display elements may also be used. For example, the lens elements 110, 112 themselves may include: a transparent or semi-transparent matrix display, such as an electroluminescent display or a liquid crystal display, one or more waveguides for delivering an image to the user's eyes, or other optical elements capable of delivering an in focus near-to-eye image to the user. A corresponding display driver may be disposed within the frame elements 104, 106 for driving such a matrix display. Alternatively or additionally, a laser or LED source and scanning system could be used to draw a raster display directly onto the retina of one or more of the user's eyes. Other possibilities exist as well.

While the wearable computing system 100 of the example embodiment illustrated in FIGS. 1A and 1B is configured as a unified package, integrated in the HMD component, other configurations are possible as well. For example, although not explicitly shown in FIGS. 1A and 1B, the wearable computing system 100 could be implemented in a distributed architecture in which all or part of the on-board computing system 118 is configured remotely from the eyeglasses 102. For example, some or all of the on-board computing system 118 could be made wearable in or on clothing as an accessory, such as in a garment pocket or on a belt clip. Similarly, other components depicted in FIGS. 1A and/or 1B as integrated in the eyeglasses 102 could also be configured remotely from the HMD component. In such a distributed architecture, certain components might still be integrated in HMD component. For instance, one or more sensors (e.g., a magnetometer, gyroscope, etc.) could be integrated in eyeglasses 102.

In an example distributed configuration, the HMD component (including other integrated components) could communicate with remote components via the communication interface 126 (or via a dedicated connection, distinct from the communication interface 126). By way of example, a wired (e.g. USB or Ethernet) or wireless (e.g., WiFi or Bluetooth) connection could support communications between a remote computing system and an HMD component. Additionally, such a communication link could be implemented between an HMD component and other remote devices, such as a laptop computer or a mobile telephone, for instance.

Figure 1C:
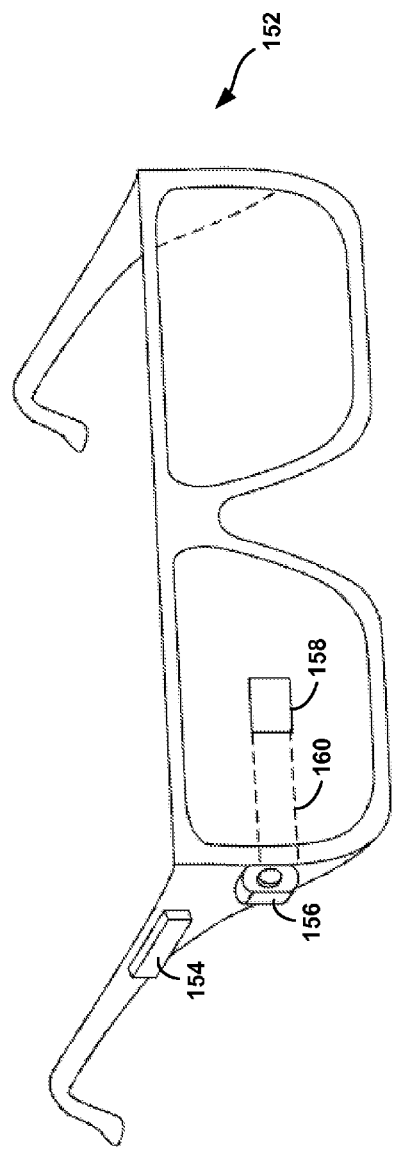
FIG. 1C illustrates another wearable computing system according to an exemplary embodiment.

FIG. 1C illustrates another wearable computing system according to an exemplary embodiment, which takes the form of an HMD 152. The HMD 152 may include frame elements and side-arms such as those described with respect to FIGS. 1A and 1B. The HMD 152 may additionally include an on-board computing system 154 and a video camera 156, such as those described with respect to FIGS. 1A and 1B. The video camera 156 is shown mounted on a frame of the HMD 152. However, the video camera 156 may be mounted at other positions as well.

As shown in FIG. 1C, the HMD 152 may include a single display 158 which may be coupled to the device. The display 158 may be formed on one of the lens elements of the HMD 152, such as a lens element described with respect to FIGS. 1A and 1B, and may be configured to overlay computer-generated graphics in the user's view of the physical world. The display 158 is shown to be provided in a center of a lens of the HMD 152, however, the display 158 may be provided in other positions. The display 158 is controllable via the computing system 154 that is coupled to the display 158 via an optical waveguide 160.

Figure 1D:
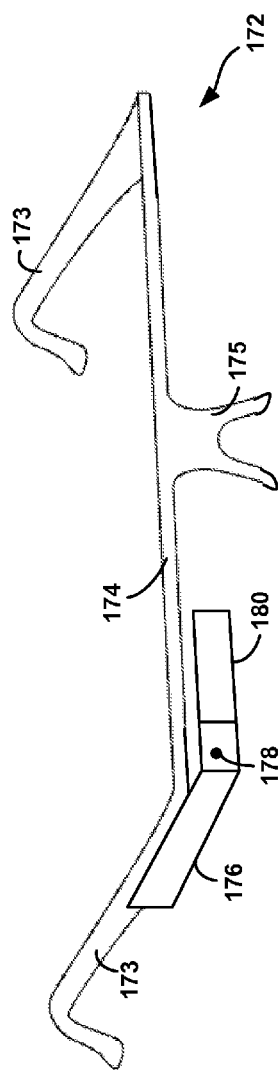
FIG. 1D illustrates another wearable computing system according to an exemplary embodiment.

FIG. 1D illustrates another wearable computing system according to an exemplary embodiment, which takes the form of an HMD 172. The HMD 172 may include side-arms 173, a center frame support 174, and a bridge portion with nose-piece 175. In the example shown in FIG. 1D, the center frame support 174 connects the side-arms 173. The HMD 172 does not include lens-frames containing lens elements. The HMD 172 may additionally include an on-board computing system 176 and a video camera 178, such as those described with respect to FIGS. 1A and 1B.

The HMD 172 may include a single lens element 180 that may be coupled to one of the side-arms 173 or the center frame support 174. The lens element 180 may include a display such as the display described with reference to FIGS. 1A and 1B, and may be configured to overlay computer-generated graphics upon the user's view of the physical world. In one example, the single lens element 180 may be coupled to the inner side (i.e., the side exposed to a portion of a user's head when worn by the user) of the extending side-arm 173. The single lens element 180 may be positioned in front of or proximate to a user's eye when the HMD 172 is worn by a user. For example, the single lens element 180 may be positioned below the center frame support 174, as shown in FIG. 1D.

FIG. 2 is a simplified illustration of a network 200 via which one or more HMDs and/or other types of computing devices, such as those illustrated in FIGS. 1A-1D, may engage in communications. As depicted, the network 200 includes a data network 202 that is connected to each of a radio access network (RAN) 204, a wireless access network 206, and a wired access network 208. The data network 202 could represent the one or more interconnected communication networks, such as or including the Internet. The radio access network 204 could represent a service provider's cellular radio network supporting, for instance, 3G and/or 4G cellular radio technologies (e.g., CDMA, EVDO, GSM, UMTS, LTE, WiMAX). The wireless access network 206 could represent a residential or hot-spot wireless area network supporting, such as, Bluetooth, ZigBee, and WiFi (e.g., 902.11a, 902.11b, 902.11g). The wired access network 208 could represent a residential or commercial local area network supporting, for instance, Ethernet.

The network 200 also includes a server system 210 connected to the data network 202. The server system 210 could represent a website or other network-based facility for providing one or another type of service to users. For instance, in accordance with an example embodiment, the server system 210 could host an online social networking service or website. As another example, the server system 210 could provide a network-based information search service. As still a further example, the server system 210 could receive eye-tracking data from an HMD, and returned analyzed results to the HMD.

FIG. 2 also shows various end-user and/or client devices connected to the network 200 via one of the three access networks. By way of example, an HMD 212 is connected to the RAN 204 via an air interface 213 (e.g., a 3G or 4G technology), and an HMD 214 is connected to the RAN 204 via an air interface 215 (e.g., a 3G or 4G technology). Also by way of example, an HMD 216 is connected to the wireless access network 206 via an air interface 217 (e.g., a WiFi technology). In addition and also by way of example, a mobile phone 218 is shown connected to the RAN 204 via an air interface 219, a smart phone 220 is shown connected to the wireless access network 206 via an air interface 221, and a laptop computer 222 is shown connected to the wired access network 208 via a wired interface 223. Each of the end-user devices could communicate with one or another network-connected device via its respective connection with the network. It could be possible as well for some of these end-user devices to communicate directly with each other (or other end-user devices not shown).

Each of the HMDs 212, 214, and 216 is depicted as being worn by different users (each user being represented by a cartoon face) in order to signify possible user-related variables, circumstances, and applications that may be associated with each HMD. For instance, the HMD 212 could at one time upload content to an online social networking service, whereas the HMD 214 could at the same or another time send a request to a network-based information search service. Users could interact with each other and/or with the network via their respective HMDs. Other examples are possible as well. For the purposes of most of the discussion herein it is usually sufficient to reference only an HMD without referencing the user (or wearer) the HMD. Explicit reference to or discussion of a user (or wearer) of an HMD will be made as necessary.

Figure 3A:
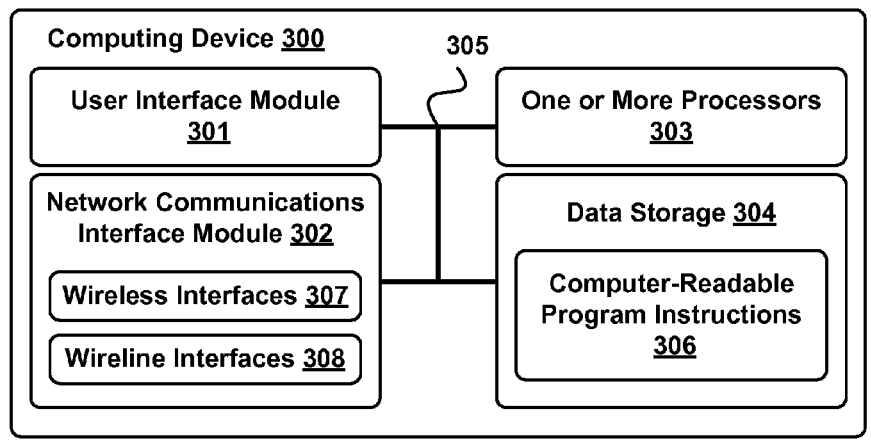
FIG. 3A is a block diagram of a computing device 300 in accordance with an exemplary embodiment.
Figure 3B:
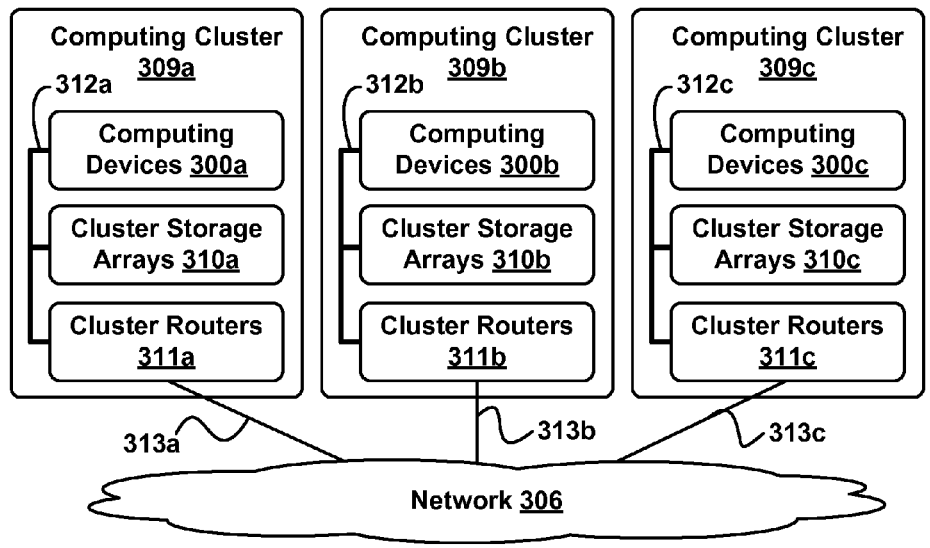
FIG. 3B depicts a network with computing clusters in accordance with an example embodiment.

A network server, such as the server system 210 in FIG. 2, could take various forms and be implemented in one or more different ways. FIGS. 3A and 3B illustrate two example embodiments of a server system: an integrated system including a representative computing device (FIG. 3A), and a distributed system (FIG. 3B) including multiple representative computing devices, as well as additional system elements, communicatively connected together.

FIG. 3A is a block diagram of a computing device 300 in accordance with an exemplary embodiment. As shown, computing device 300 includes a user interface module 301, a network-communication interface module 302, one or more processors 303, and data storage 304, all of which can be linked together via a system bus, network, or other connection mechanism 305. The computing device 300 may be any type of device that can receive data and provide information for display in association with the received data. For example, the device 300 may take the form of or be included as part of a wearable computing device, such as the head-mounted devices 102, 152, or 172 described with reference to FIGS. 1A-1D. Further, as noted above, computing device 300 could also take the form of or be included in an integrated server system. Computing device 300 may take other forms and/or be included as part of other systems as well.

The user interface module 301 can be operable to send data to and/or receive data from external user input/output devices. For example, the user interface module 301 can be configured to send/receive data to/from user input devices such as a keyboard, a keypad, a touch screen, a computer mouse, a track ball, a joystick, and/or other similar devices, now known or later developed. The user interface module 301 can also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interface module 301 can also be configured to generate audible output(s), such as a speaker, speaker jack, audio output port, audio output device, earphones, and/or other similar devices, now known or later developed.

The network-communications interface module 302 can include one or more wireless interfaces 307 and/or wireline interfaces 308 that are configurable to communicate via a network, such as the network 202 shown in FIG. 2. The wireless interfaces 307 can include one or more wireless transceivers, such as a Bluetooth transceiver, a Wi-Fi transceiver perhaps operating in accordance with an IEEE 902.11 standard (e.g., 902.11a, 902.11b, 902.11g), a WiMAX transceiver perhaps operating in accordance with an IEEE 902.16 standard, and/or other types of wireless transceivers configurable to communicate via a wireless network. The wireline interfaces 308 can include one or more wireline transceivers, such as an Ethernet transceiver, a Universal Serial Bus (USB) transceiver, or similar transceiver configurable to communicate via a wire, a twisted pair of wires, a coaxial cable, an optical link, a fiber-optic link, or other physical connection to a wireline network.

In some embodiments, the network communications interface module 302 can be configured to provide reliable, secured, compressed, and/or authenticated communications. For each communication described herein, information for ensuring reliable communications (e.g., guaranteed message delivery) can be provided, perhaps as part of a message header and/or footer (e.g., packet/message sequencing information, encapsulation header(s) and/or footer(s), size/time information, and transmission verification information such as cyclic redundancy check (CRC) and/or parity check values). Communications can be compressed and decompressed using one or more compression and/or decompression algorithms and/or protocols such as, but not limited to, one or more lossless data compression algorithms and/or one or more lossy data compression algorithms. Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well or in addition to those listed herein to secure (and then decrypt/decode) communications.

The one or more processors 303 can include one or more general purpose processors and/or one or more special purpose processors (e.g., digital signal processors, application specific integrated circuits, etc.). The one or more processors 303 can be configured to execute computer-readable program instructions 306 that are contained in the data storage 304 and/or other instructions as described herein.

The data storage 304 can include one or more computer-readable storage media that can be read or accessed by at least one of the processors 303. The one or more computer-readable storage media can include volatile and/or non-volatile storage components, such as optical, magnetic, organic or other memory or disc storage, which can be integrated in whole or in part with at least one of the one or more processors 303. In some embodiments, the data storage 304 can be implemented using a single physical device (e.g., one optical, magnetic, organic or other memory or disc storage unit), while in other embodiments, the data storage 304 can be implemented using two or more physical devices.

Computer-readable storage media associated with data storage 304 and/or other computer-readable media described herein can also include non-transitory computer-readable media such as computer-readable media that stores data for short periods of time like register memory, processor cache, and random access memory (RAM). Computer-readable storage media associated with data storage 304 and/or other computer-readable media described herein can also include non-transitory computer readable media that stores program code and/or data for longer periods of time, such as secondary or persistent long term storage, like read only memory (ROM), optical or magnetic disks, compact-disc read only memory (CD-ROM), for example. Computer-readable storage media associated with data storage 304 and/or other computer-readable media described herein can also be any other volatile or non-volatile storage systems. Computer-readable storage media associated with data storage 304 and/or other computer-readable media described herein can be considered computer readable storage media for example, or a tangible storage device.

The data storage 304 can include computer-readable program instructions 306 and perhaps additional data. In some embodiments, the data storage 304 can additionally include storage required to perform at least part of the herein-described techniques, methods, and/or at least part of the functionality of the herein-described devices and networks.

FIG. 3B depicts a network 306 with computing clusters 309a, 309b, and 309c in accordance with an example embodiment. In FIG. 3B, functions of a network server, such as the server system 210 in FIG. 2, can be distributed among three computing clusters 309a, 309b, and 308c. The computing cluster 309a can include one or more computing devices 300a, cluster storage arrays 310a, and cluster routers 311a, connected together by local cluster network 312a. Similarly, computing cluster 309b can include one or more computing devices 300b, cluster storage arrays 310b, and cluster routers 311b, connected together by local cluster network 312b. Likewise, computing cluster 309c can include one or more computing devices 300c, cluster storage arrays 310c, and cluster routers 311c, connected together by a local cluster network 312c.

In some embodiments, each of computing clusters 309a, 309b, and 309c can have an equal number of computing devices, an equal number of cluster storage arrays, and an equal number of cluster routers. In other embodiments, however, some or all of computing clusters 309a, 309b, and 309c can have different numbers of computing devices, different numbers of cluster storage arrays, and/or different numbers of cluster routers. The number of computing devices, cluster storage arrays, and cluster routers in each computing cluster can depend on the computing task or tasks assigned to each computing cluster.

Cluster storage arrays 310a, 310b, and 310c of computing clusters 309a, 309b, and 309c can be data storage arrays that include disk array controllers configured to manage read and write access to groups of hard disk drives. The disk array controllers, alone or in conjunction with their respective computing devices, can also be configured to manage backup or redundant copies of the data stored in the cluster storage arrays to protect against disk drive or other cluster storage array failures and/or network failures that prevent one or more computing devices from accessing one or more cluster storage arrays.

The cluster routers 311a, 311b, and 311c in the computing clusters 309a, 309b, and 309c can include networking equipment configured to provide internal and external communications for the computing clusters. For example, the cluster routers 311a in the computing cluster 309a can include one or more internet switching and/or routing devices configured to provide (i) local area network communications between the computing devices 300a and the cluster storage arrays 301a via the local cluster network 312a, and/or (ii) wide area network communications between the computing cluster 309a and the computing clusters 309b and 309c via the wide area network connection 313a to the network 306. The cluster routers 311b and 311c can include network equipment similar to the cluster routers 311a, and the cluster routers 311b and 311c can perform similar networking functions for the computing clusters 309b and 309b that the cluster routers 311a perform for the computing cluster 309a.

III. EXEMPLARY METHODS

A. Exemplary HMD-Implemented Methods

Figure 4:
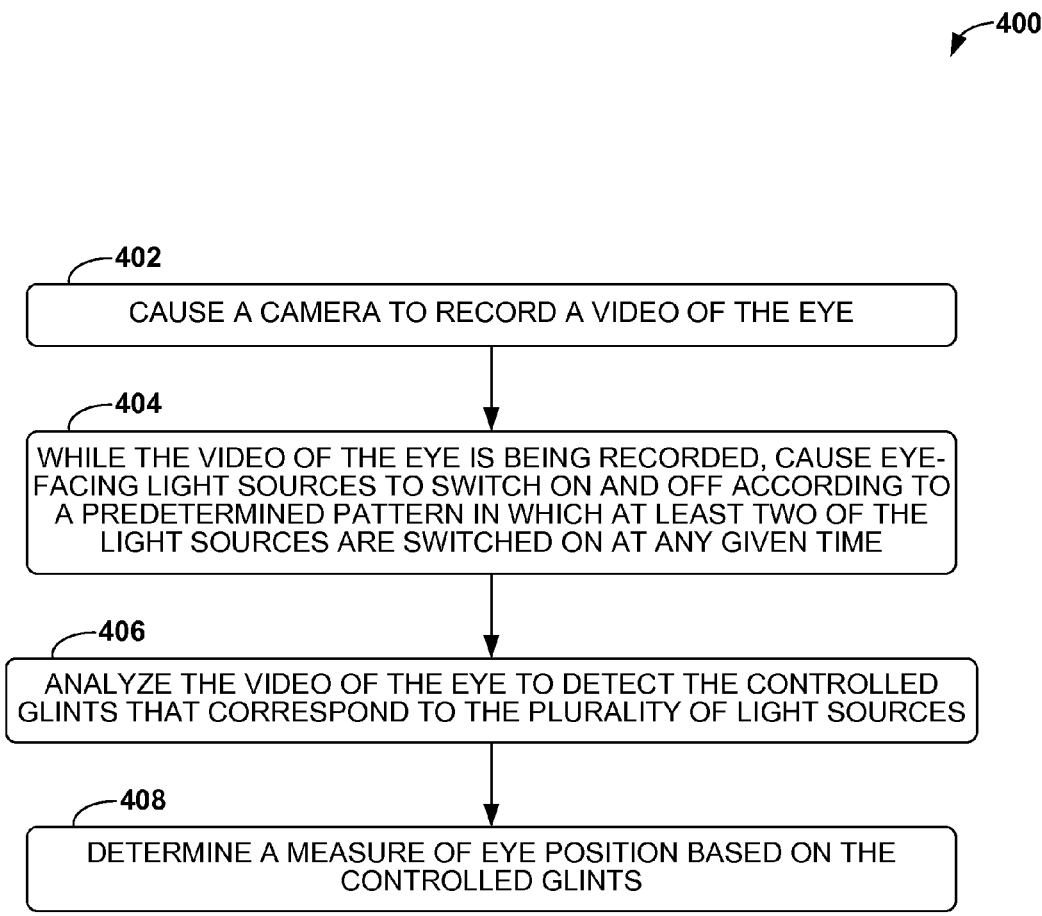
FIG. 4 is a flow chart illustrating a method 400, according to an exemplary embodiment.

FIG. 4 is a flow chart illustrating a method 400, according to an exemplary embodiment. Exemplary methods, such as method 400, may be carried out in whole or in part by a wearable computer having a head-mountable display (which may further have an inward-facing camera, depending upon the particular implementation). For simplicity, a wearable computer configured as such may simply be referred to as a "head-mountable display" or "HMD" herein.

As shown by block 402 of FIG. 4, exemplary method 400 involves an HMD causing a camera that is attached to the HMD to record a video of the eye. While the video of the eye is being recorded, the HMD causes a number (e.g., three or more) of eye-facing light sources, which may be attached to the HMD, to switch on and off according to a predetermined pattern in which at least two of the light sources are switched on at any given time while the video of the eye is being recorded, as shown by block 404. The HMD may then analyze the video of the eye to detect the controlled glints that correspond to the plurality of light sources, as shown by block 406. Then, the HMD may determine a measure of eye position based on the controlled glints, as shown by block 408.

i. Switching Light Sources on and Off According to a Predetermined Pattern

As noted above, at block 404, the light sources are switched on and off according to a predetermined pattern in which at least two light sources are switched on at any given point while the video is being recorded. (Note that this does allow prevent instances where less than two light sources are switched on, in between frames of the video.) As a general example, such a predetermined pattern may involve switching off just one of the light sources at a given time and changing the switched-off light source one or more times while the video of the eye is being recorded, according to a predefined schedule. Other general examples are also possible.

In some embodiments, the predetermined pattern may be a predetermined sequence of light-source combinations, with each combination having certain light sources that are turned on. Further, in such an embodiment, the sequence of light-source combinations may be repeated.

Figure 5A:
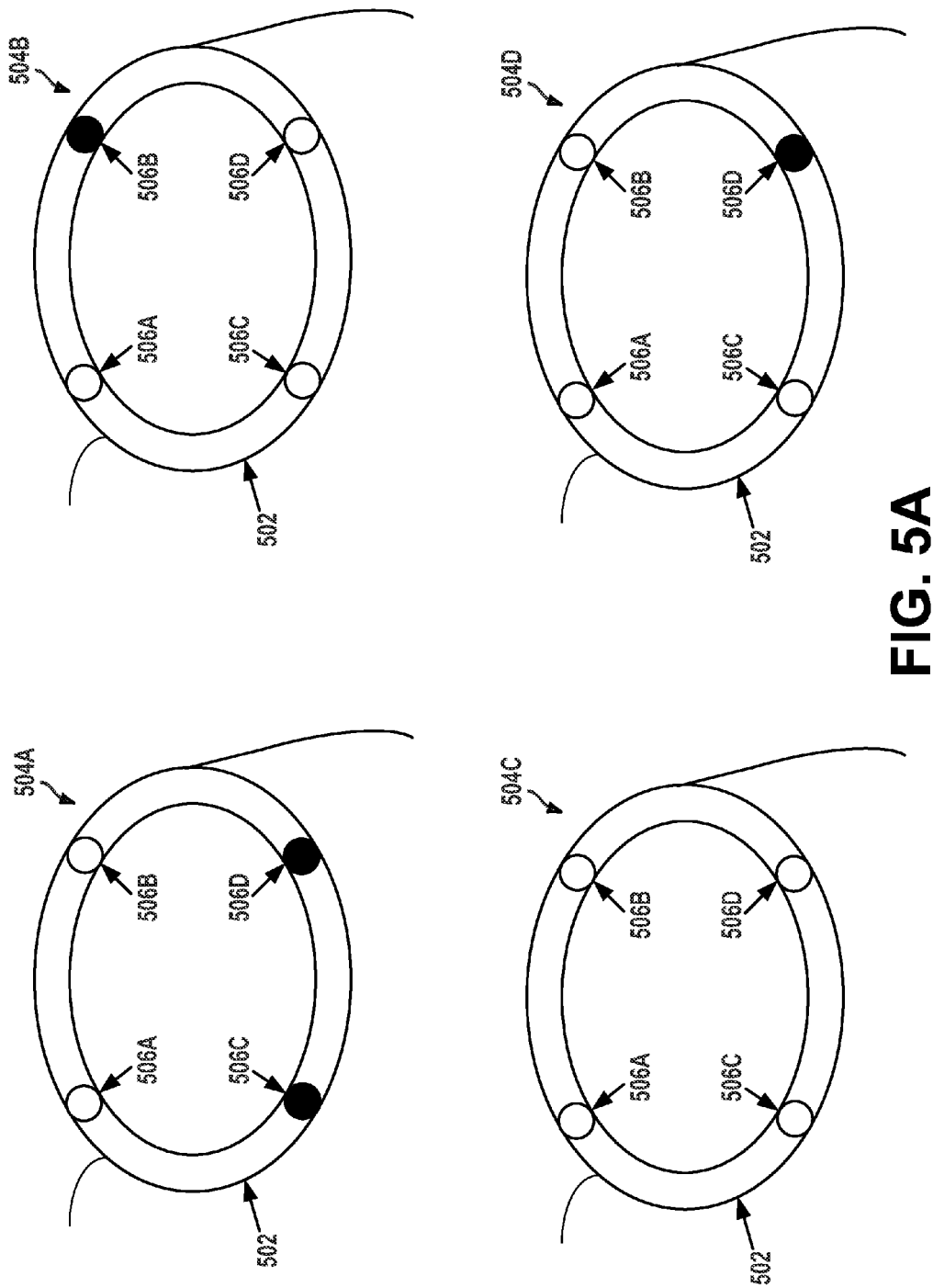
FIG. 5A is a simplified illustration of a predetermined sequence of light-source combinations, according to an exemplary embodiment.

FIG. 5A is a simplified illustration of a predetermined sequence of light-source combinations, according to an exemplary embodiment. Specifically, FIG. 5A shows an HMD 502 going through a sequence of four light-source combinations 504A to 504D. To do so, HMD 502 includes four light sources 506A to 506D, which are attached to the frame of HMD 502 in a substantially rectangular arrangement relative to one another. Configured as such, HMD 502 may individually switch light sources 506A to 506D on and off according to a predetermined pattern. (Note that for purposes of illustration in FIGS. 5A and 6, switched-off light sources are black and switched-on light sources are white.)

In the illustrated embodiment, the predetermined pattern may be the sequence of light-source combinations 504A to 504D. As such, the HMD 502 may initially turn on light sources 506A and 506B in order to form light-source combination 504A. Then, after a predetermined period of time, the HMD may turn on light sources 506A, 506C, and 506D to form light-source combination 504B. After again waiting the predetermined period of time, the HMD 502 may turn on all the light sources 506A to 506D to form light-source combination 504C. Next, and again after waiting the predetermined period of time, HMD 502 may turn on light sources 506A to 506C to form light-source combination 504D. Further, the HMD 502 may repeat the above cycle of light-source combinations 504A to 504D one or more times.

ii. Analyzing the Video to Detect Controlled Glints

Since the timing with which the sequence of light-source combinations is displayed is generally known, an HMD may know which glints to search for when analyzing the video of the eye for controlled glints. More specifically, at block 406 of method 400, the HMD may analyze individual frames of the video for controlled glints captured in each frame. To do so, the HMD may first determine which light sources were switched on when a given frame was recorded (e.g., by determining what combination in the sequence was formed when the frame was recorded). As such, the HMD can more efficiently analyze the frame by searching for just the controlled glints that correspond to the light sources that were switched on when the frame was recorded.

In a further aspect, to help locate the glints in an image of the eye, the HMD may compare two or more images (e.g., two or more video frames). For example, the HMD may subtract two frames with different, known, light-source combinations. More specifically, by subtracting a frame where a given light source is switched on from a frame where the light source is switched off, the HMD may better determine the location of the corresponding glint in the frame where the light source is switched on.

Figure 5B:
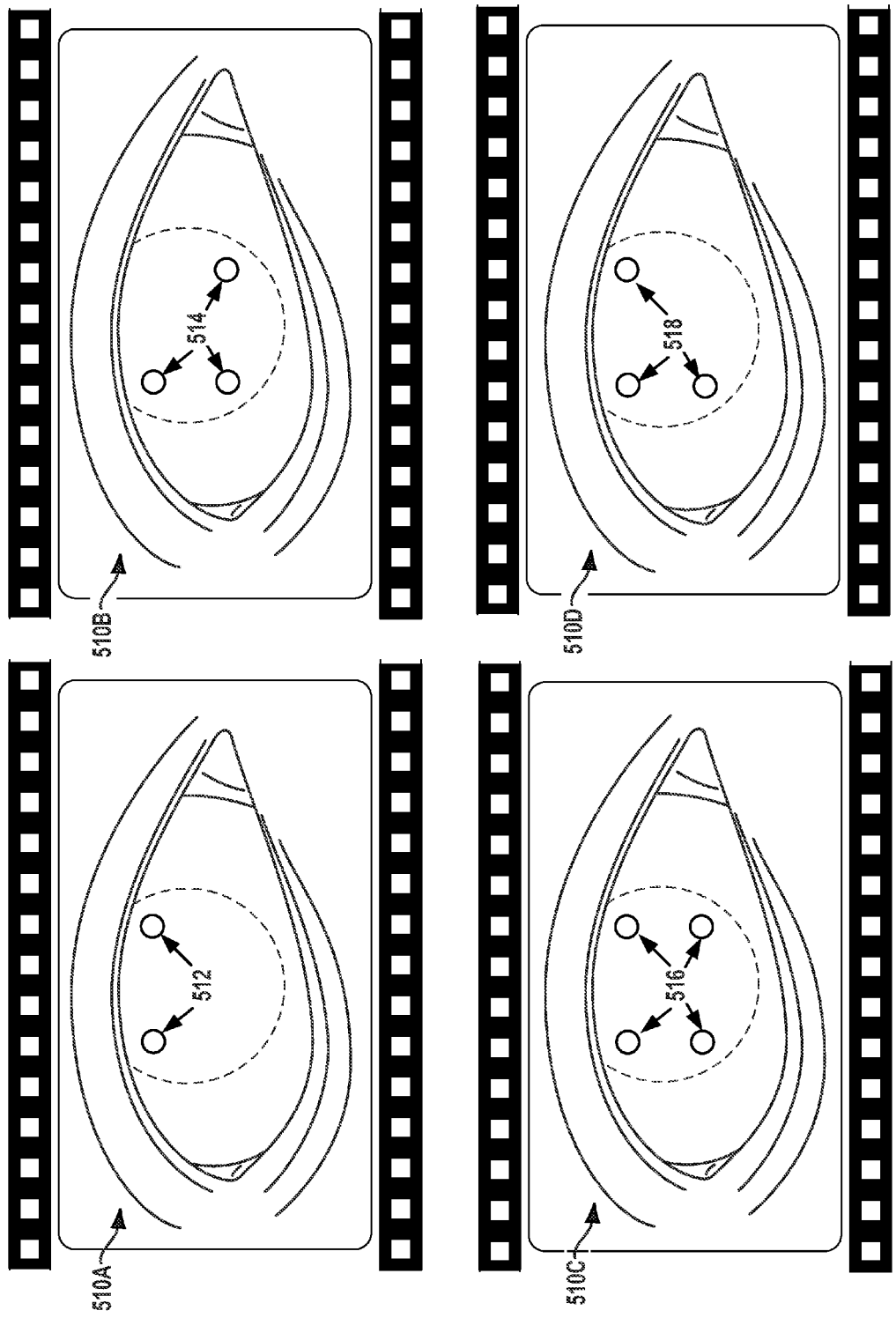
FIG. 5B is a simplified illustration of frames from a video of the eye that is captured during the sequence of light-source combinations shown in FIG. 5A, according to an exemplary embodiment.

FIG. 5B is a simplified illustration of frames from a video of the eye that is captured during the sequence of light-source combinations shown in FIG. 5A, according to an exemplary embodiment. In particular, frames 510A to 510D capture controlled the glints that correspond to light-source combinations 504A to 504D, respectively.

More specifically, frame 510A captures controlled glints 512 that correspond to light-source combination 504A (i.e., controlled glints that result from light sources 506A and 506B reflecting off the eye). Similarly, frame 510B captures controlled glints 514 that correspond to light-source combination 504B (i.e., controlled glints corresponding light sources 506A, 506C, and 506D), frame 510C captures controlled glints 516 that correspond to light-source combination 504C (i.e., controlled glints corresponding all light sources 506A to 506D), and frame 510D captures controlled glints 518 that correspond to light-source combination 504D (i.e., controlled glints corresponding light sources 506A to 506C).

Note that in some embodiments, light-sources forming one light-source combination in a sequence may be left on until it is time for the next light-source combination in the sequence. In such an embodiment, a light source that is switched on in consecutive light-source combinations in the predetermined sequence may simply be left on when the HMD switches from the first of the consecutive combinations to the second. For example, in such an embodiment, switching from light-source combination 504A to light-source combination 504B may involve switching off light source 506B, switching on light sources 506C and 506D, and simply leaving light source 506A switched on. Other examples are also possible.

In other embodiments, an HMD may turn off all light sources in between light-source combinations in the sequence. For example, the HMD may turn on the light sources for a given combination for a certain period of time and then turn off all the light sources for a certain period of time before turning on the light source that form the next combination in the sequence.

Note that the period for which each combination is formed and/or the period for which the HMD turns off all light sources between combinations in the sequence may vary, depending upon the particular implementation. For instance, in some implementations, the HMD 502 may flash light-source combinations such that each light-source combination is formed for a short period, with the light sources otherwise being turned off. By turning off the light sources in between combinations in the sequence, such an implementation may help to conserve power and/or may provide other benefits.

Further, in such an implementation, the timing with which the HMD flashes the light-source combinations may be substantially phase-synchronized with the frames of the video that is capturing the eye. For example, the light-source combinations may be flashed such that glints corresponding to the switched-on light sources are captured in each video frame. To do so, the sequence of light-source combinations may be timed according to the frame rate of the video, such that the HMD forms the next combination in the sequence before the next frame in the video of the eye is captured. Thus, for any two consecutive frames in the video of the eye, the light-source combination that is formed when the first of two consecutive frames is recorded will differ from the light-source combination that is formed when the second of the consecutive frames is recorded.

In some embodiments, the predetermined pattern with which the light sources are switched on and off may be such that no more than one light source is switched off in any given light-source combination. Since having more light sources generally results in having more controlled glints that can be used to determine eye position, increasing the number of switched on light sources when a given image of the eye is captured may improve the accuracy with which eye position can be measured based on the corresponding glints. Thus, a sequence of light-source combinations in which no more than one light source is switched off in any given combination, may facilitate more accurate eye tracking than a sequence that includes combinations with more than one light source switched off.

FIG. 6 is a simplified illustration of a predetermined sequence of light-source combinations, according to an exemplary embodiment. Specifically, FIG. 6 illustrates a sequence of light-source combinations 604A to 604D in which no more than one light source is switched off in any given combination. More specifically, in the first light-source combination 604A in the sequence, light source 606A is switched off, while light sources 606B, 606C, and 606D are switched on. In the second light-source combination 604B in the sequence, light source 606B is switched off, while light sources 606A, 606C, and 606D are switched on. In the third light-source combination 604C in the sequence, light source 606C is switched off, while light sources 606A, 606B, and 606D are switched on. Lastly, in the fourth light-source combination 604D in the sequence, light source 606D is switched off, while light sources 606A, 606B, and 606C are switched on.

It should be understood that the examples in FIGS. 5A, 5B, and 6 are provided for illustrative purposes, and that numerous variations on the illustrated examples and other examples are possible. For instance, while FIGS. 5A, 5B, and 6 illustrate an HMD with four light sources arranged in a rectangular relationship, the number of light sources and arrangement of light sources on the HMD may vary. Further, while FIGS. 5A, 5B, and 6 illustrate examples in which the predetermined pattern takes the form of a sequence of four light-source combinations, the number of light source combinations in such a sequence may vary, without departing from the scope of the invention. Other examples and variations on the above described examples are possible as well.

iii. Determining Eye Position Based on Controlled Glints

Referring back to blocks 406 and 408 FIG. 4, an HMD may use various techniques to determine a measure of eye position based on the detected glints. In particular, the HMD may determine an eye position on a frame by frame basis. Thus, as each frame is evaluated, the HMD may determine the eye position at the time the frame was recorded.

For example, at block 406 of method 400, the HMD may have determined which light sources were switched on when a given frame was recorded (e.g., the light-source combination corresponding to the frame) and, if analysis of the frame is successful, will have detected controlled glints that correspond to the particular light-source combination. As such, to determine eye position at block 408, the HMD may determine the spatial relationship between the controlled glints that are detected in a given frame, and then determine an eye position based on this spatial relationship.

In particular, the spatial relationship between controlled glints in a frame may vary depending upon the position of the eye. More specifically, since the light sources are generally fixed, but the curvature of the surface of the eye is such that the distance from the surface of the eye to a fixed light source will typically vary as the eye rotates within the orbit. Thus, the angle at which the light source reflects from the surface of the eye (e.g., from the cornea and/or sclera) may vary depending upon the position of the eye. Therefore, when multiple fixed light sources are directed towards the eye, the spatial relationship between the glints corresponding to the light sources may vary, depending upon the respective angles of reflection that result from the current eye position. More details of such a method (albeit without any variation in which light sources are switched on and off) are described in Hammoud, Passive Eye Monitoring, pp. 136-141, 202-204. Another possible method is described in Nagamatsu, *Gaze Estimation Method Based on an Aspherical Model of the Cornea: Surface of Revolution about the Optical Axis of the Eye*, Proceeding of the 2010 Symposium on Eye-Tracking Research & Applications, pp. 255-258 (ACM 2010).

In a further aspect, by determining the eye position over the course of a video with multiple frames, the HMD may evaluate eye movement during the time when the video was recorded. For example, to determine eye movement, the HMD may determine the change in eye position over the two or more frames of the video. The HMD may then quantify the change in position by, e.g., determining an eye-movement value (e.g., an angular movement of the eye in the orbit) that corresponds to the change in eye position over the two or more frames of the video. Other examples are also possible.

It should be understood that while exemplary methods such as method 400 are described by way of example as being implemented by an HMD, an exemplary method may also be implemented in whole or in part by other types of computing devices. For example, an exemplary method may be implemented in whole or in part by a mobile phone, a tablet computer, a laptop or desktop computer equipped with a camera, and/or a network-enabled camera. Other examples of computing devices or combinations of computing devices that can implement an exemplary method are possible. In general, an exemplary method may be implemented by any computing device, system, or combinations of computing device(s) and/or system(s) that are configured to provide the same or similar functions as described herein.

B. Exemplary Cloud-Based Methods

As noted above, an exemplary method may also be carried out in whole or in part by a device or system, or by a combination of one or more devices and/or one or more systems, which are in communication with and can receive eye-tracking data from a device or system that captures the eye tracking data (e.g., an HMD). For example, an exemplary method may be implemented in whole or in part by a server system, which receives data from a device such as an HMD.

Figure 7:
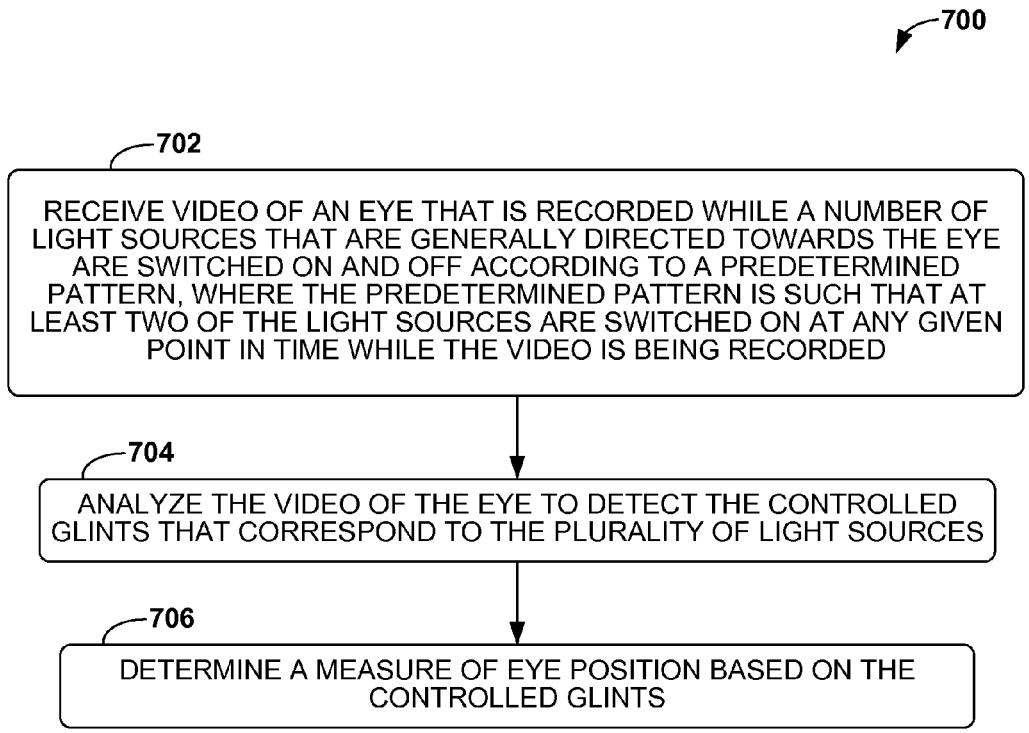
FIG. 7 is a flow chart illustrating a method that may be carried out by a server system, according to an exemplary embodiment.

FIG. 7 is a flow chart illustrating a method that may be carried out by a server system, according to an exemplary embodiment. It should be understood that while method 700 is described by way of example as being carried out by a server system (e.g., a cloud-based server), other device(s) and/or system(s) may carry out a method such as method 700, without departing from the scope of the invention.

As illustrated by block 702, an exemplary method 700 may involve a server system receiving video of an eye that is recorded while a number of light sources that are generally directed towards the eye are switched on and off according to a predetermined pattern, where the predetermined pattern is such that at least two of the light sources are switched on at any given point in time while the video is being recorded. The server system then analyzes the video of the eye to detect controlled glints that correspond to the plurality of light sources, as shown by block 704. The server system then determines a measure of eye position based on the controlled glints, as shown by block 706.

IV. ADDITIONAL ASPECTS

Some embodiments may generally relate to camera-based eye tracking systems that estimate a user's gaze by comparing the pupil location to the relative location of a glint on the user's cornea. In such systems, the tracking algorithms can compensate for movement of the user's head relative to the camera; e.g., if the wearer is looking at a target in the environment and the wearer moves their head, but keeps their gaze substantially fixed on the target, then the wearer's eye will move in the wearer's orbit (e.g., rotate in the eye socket). As such, the position of the eye can be approximated by determining a vector from the pupil center and a glint reflection off of the user's cornea.

In some instances, sunlight or other light sources in the environment can create glints that can confuse the tracker. Some systems will compensate for ambient light glints by using active illumination; e.g., strobing the light sources and differencing two camera frames to isolate the glint of interest. Because the system may require that the eye be well illuminated for both frames, a secondary light source (global illumination) may be provided. The global illumination will create a secondary glint which should be removed from the frames to help improve tracking By providing three or more (and preferably five or more) glints, software may provide calibration that compensates for translation, rotation and scale shifts.

Accordingly, some embodiments may provide an eye tracker in a head mounted display system that uses, e.g., four IR LEDS to provide both global illumination of the eye and four glint locations in every camera frame. The four LEDs may be oriented in a square pattern to reflect off the user's cornea, and for each video frame one of the LEDs may be turned off or on. The toggling order of the LEDs may be fixed, for example, in either a clockwise or an anti-clockwise rotation. This hardware design may help to reduce the ambiguity and uncertainty for glint tracking software. Further, frame differencing may help to allow all of the LEDs to be more robustly detected and/or identified when ambient noise (e.g., ambient glints) exists. Tracking algorithms may thus compare the user's pupil center and glint locations in order to have the tracking model dynamically adapt to shifts of the camera and display (HMD) on the user's face (e.g., device drift.)

In such an embodiment, the camera and display can be attached to a common frame so that they do not move independently of each other. However, note that this and other embodiments may apply to other eye-tracking systems, including ones that are not on HMDs.

V. Glint Detection and Gaze-Tracking System Based Thereon

Figure 8:
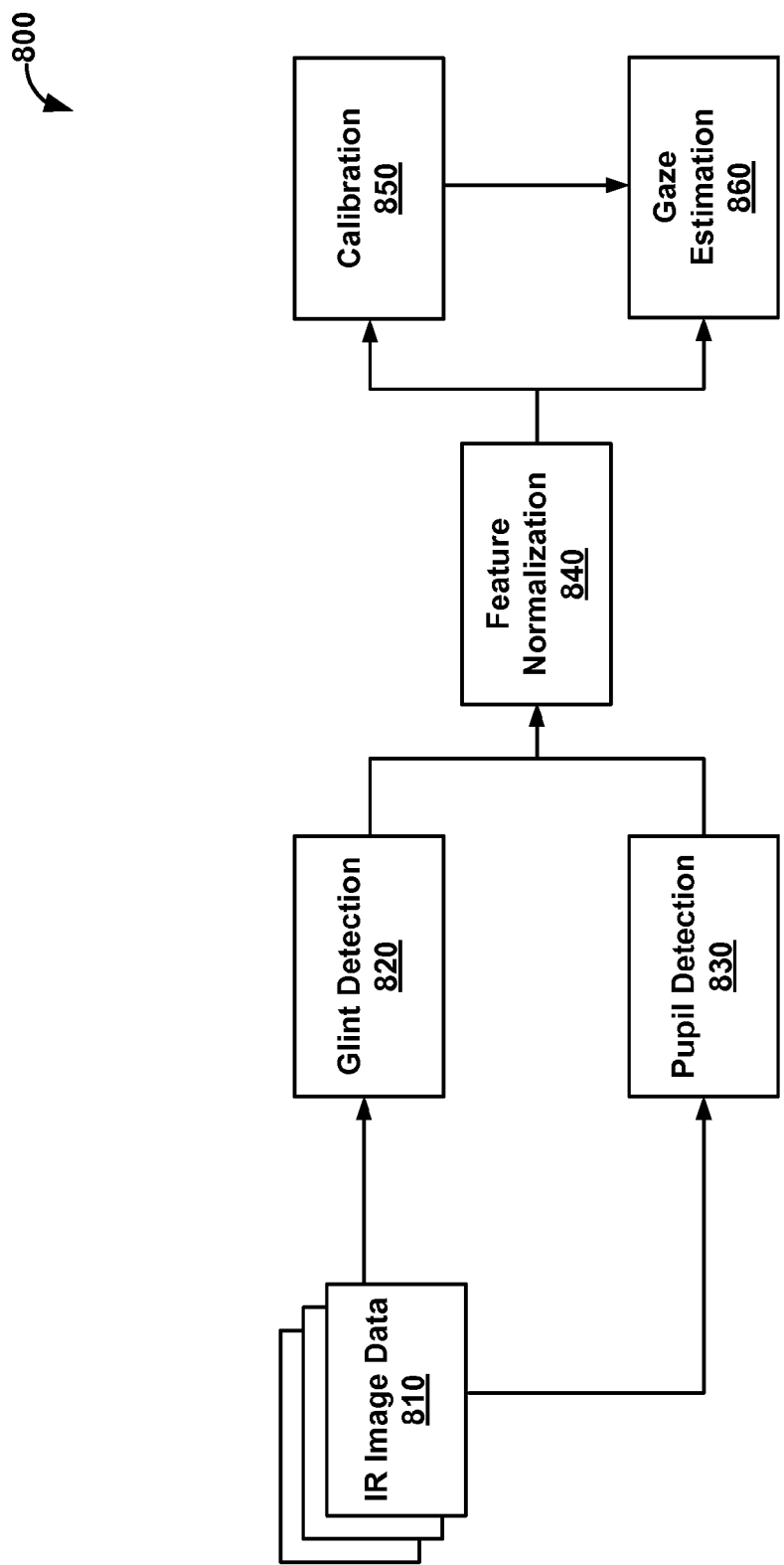
FIG. 8 is a simplified illustration of a gaze-tracking system 100, according to an illustrative embodiment.

FIG. 8 is a simplified illustration of a gaze-tracking system 100, according to an illustrative embodiment. The system may include software, hardware and/or firmware. As shown, system 100 includes a glint detection module (GDM) 820, a pupil detection module (PDM) 830, a feature normalization module 840, a calibration module 850, and a gaze estimation module 860. Further, GDM 820 and PDM 830 are configured to receive IR image data 810.

The IR image data 810 may take various forms. For example, IR image data 810 may be video captured by a single, or possibly multiple IR cameras. Further, the IR camera may be configured, and/or the IR image data may be processed, such that the video includes a sequence of gray scale images of an eye. Other types of IR image data are also possible.

Further, a number of IR light sources (e.g., four IR LEDS) may be attached to an HMD or otherwise arranged so as to direct light towards the eye and create glints on the retina. Glint detection module 820 may be configured to analyze the IR image data 810 and detect the glints, which may then be utilized to normalize pupil location as determined by pupil detection module 830.

Glint detection module 820 may use various techniques to determine and/or track the location of glints. For example, glint detection module 820 may utilize a motion-detection-based technique to detect and track glints in IR image data 810, such as the technique that is described in greater detail below in section VI(A).

The pupil detection module 830 may use various techniques to determine and/or track the location of the pupil; and in particular, to determine the location of the center of the pupil. For example, pupil detection module 830 may utilize a computer-vision algorithm to estimate the coordinates of the pupil center. Further, in some embodiments, the determined coordinates may be adjusted based on a balloon-blowing algorithm. This process is described in greater detail below in section VI(B). However, it should be understood that other pupil-detection techniques and/or other techniques for locating the center of the pupil are also possible.

Feature normalization module 840 may use various techniques to normalize pupil location based on detected glints. For example, as described in greater detail in section VI(C), feature normalization module 840 may determine a normalized feature vector for each frame of IR image data by using the glint locations for the frame, as determined by glint detection module 820, to normalize the pupil-center location, as determined by pupil detection module 830. This may help to eliminate or reduce the amount of calibration required by system 800 and/or may help to improve the ability of system 800 to provide accurate gaze tracking when drift of the head occurs.

Calibration module 850 may use various techniques to calibrate data associated with one or more inputs. For example, as described in greater detail in section VI(D), calibration module 850 may receive an expected gaze location and a normalized pupil location as inputs. The calibration module 850 may use the inputs to train one or more regressors using different combinatoric sub-sets of the glints for normalization. The result of the calibration may include an ensemble of polynomial regressors, which may be used to more effectively determine an estimated gaze location.

Gaze estimation module 860 may use various techniques to determine an estimated gaze location. For example, as described in greater detail in section VI(E), gaze estimation module 860 may receive one or more of the polynomial regressors from the calibration module 850. The gaze estimation module 860 may combine the regressors to estimate a gaze location for one or more frames. As an example, the gaze estimation module 860 may combine multiple regressors to determine a median gaze location over a predetermined number of frames. In a further aspect, the estimated gaze location may be presented to the user to verify the gaze estimation quality after calibration.

A. Glint Detection

In an example embodiment, glint detection module 820 may analyze IR image data 810 to output the locations of glints in the image data. In particular, the glint detection module 820 may output one or more estimates of the image coordinates for each glint. Each estimate may also be referred to as a "glint hypothesis," while a set of one or more estimates for a given glint may be referred to as the "glint hypothesis set" for the given glint.

Figure 9:
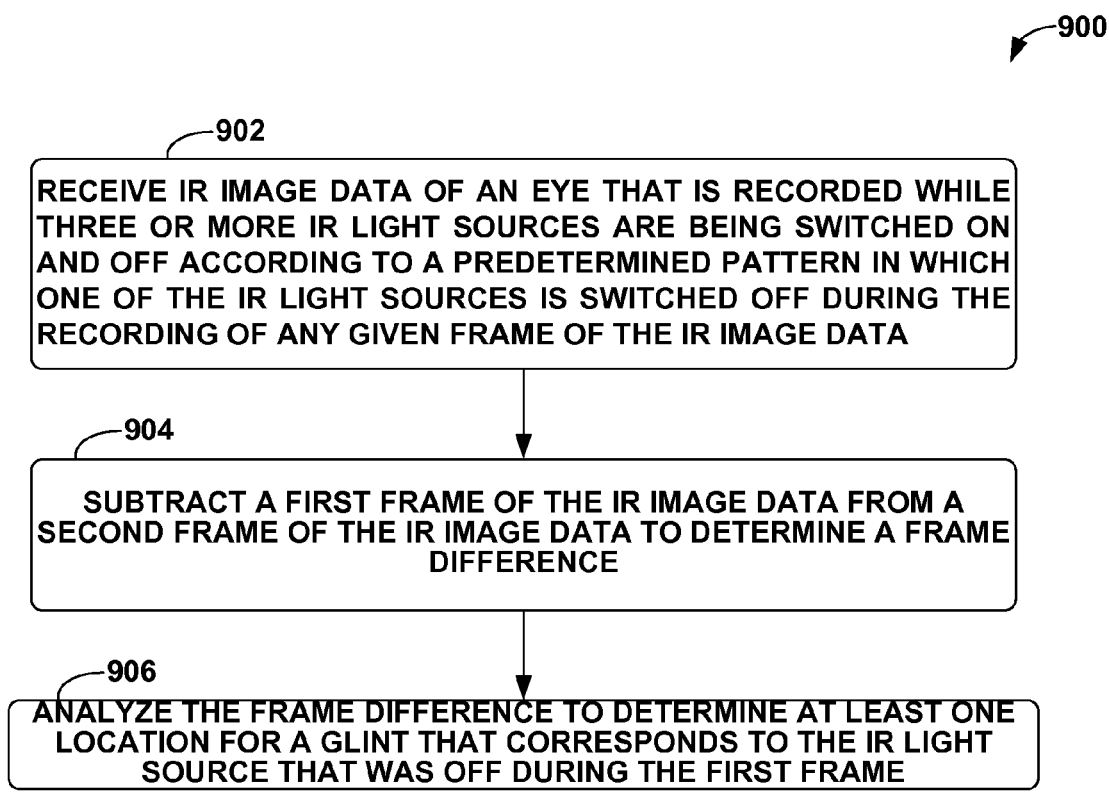
FIG. 9 is a flow chart illustrating a method 900 for glint detection, according to an example embodiment.

FIG. 9 is a flow chart illustrating a method 900 for glint detection, according to an example embodiment. Method 900 is described by way of example as being carried out by GDM 820. It should be understood that functions described as being carried out by GDM may be carried out by the software, hardware, and/or firmware that are used to implement a glint detection module. Further, other devices, systems, or components thereof may carry out an example methods or portions thereof without departing from the scope of the invention.

As shown by block 902, method 900 involves the GDM 820 receiving infrared IR image data 810 of an eye. The IR image data may be, for example, video or a sequence of still images of the eye. Further, three or more IR light sources are arranged to direct light towards the eye, and the IR image data may capture the glint or glints that result from when the IR light sources are switched on. More specifically, at block 902, the IR image data may be recorded while three or more IR light sources are being switched on and off according to a predetermined pattern in which one of the IR light sources is switched off during the recording of any given frame of the IR image data.

At block 904, the GDM subtracts a first frame of the IR image data from a second frame of the IR image data to determine a first frame difference. The GDM may then analyze the first frame difference to determine at least one location for a first glint corresponding to a first one of the IR light sources, which was off during the first frame (and is on during the second frame), as shown by block 906.

Method 900 will know be described by way of example with reference to an implementation in which four glints can be created by four IR light sources, and in the IR light sources are arranged such that the four glints form a rectangular glint pattern. However, it should be understood that embodiments may be implemented with more or less glints and/or with differently-shaped glint patterns.

FIGS. 10A and 10B illustrate a first frame and a second frame of IR image data, respectively, according to an illustrative scenario. In particular, FIG. 10A shows a first frame 1010 from a sequence of IR images of the eye, and FIG. 10B shows a second frame 1020 from the sequence. In the illustrated scenario, one IR light source is switched off for each frame, with the particular IR light source that is switched off being rotated in a clockwise direction. As such, the first frame 1010 captures glints A, B, and C. In the second frame 1020, the switched off light source is rotated such glint D appears, while glint A disappears and thus is not captured. As such, the second frame 1020 captures glints B, C, and D.

Note that the second frame 1020 also includes glints X, Y, and Z, which do not correspond to any of the IR light sources. Other glints, such as glints X, Y, and Z may result from other light sources in the environment (e.g., the sun, a desk lamp, a computer monitor, etc.).

According to method 900, GDM 820 may receive the first frame 1010 and the second frame 1020, and determine a frame difference between the two frames. In an example embodiment, GDM 820 may further apply a binary threshold process to filter the frame difference. By doing so, the GDM may substantially remove disappearing glints the frame difference. Note that herein disappearing glints should be understood to be glints that appear in the one frame and are not in a subsequent frame (due to the corresponding light source being switched on and off).

i. Hypothesis Set for an Appearing Glint

FIG. 10C is a simplified illustration of a frame difference 1030, according to an illustrative embodiment. In particular, frame difference 1030 may be a thresholded frame difference that is determined by subtracting the first frame 1010 from the second frame 1020, and applying binary thresholding to the resulting frame difference. Thus, as shown, thresholded frame difference 1030 includes glint D, which is the appearing glint in the second frame 1020.

In the illustrated scenario, thresholded frame difference 1030 also includes glints X, Y, and Z, which result from, e.g., ambient light sources. Glints that do not correspond to an IR light source (e.g., that are not controlled), such as glints X, Y, and Z, may be referred to as "ambient glints." In some instances, ambient glints may interfere with the detection of the glint pattern from the IR light sources. Therefore, in some embodiments, GDM 820 may implement various techniques to determine which glints correspond to IR light sources (e.g., which glints are controlled) and/or which glints are ambient glints. Further, GDM 820 may filter out ambient glints from image data (e.g., from a frame difference).

For example, GDM 820 may analyze the thresholded frame difference 1030 to identify glints D, X, Y, and Z as "glint candidates" (e.g., candidates to be labeled as a controlled glint corresponding to an IR light source). GDM 820 may then apply shape criteria to each of the glint candidates D, X, Y, and Z to determine a subset of glint candidates that meet the shape criteria. For example, the shape criteria may specify a certain expected size and/or shape of a controlled glint (e.g., a round or circular shape having a radius that is expected of a controlled glint), as well as an acceptable deviation from the expected size and/or shape. Other examples of shape criteria are also possible.

Applying illustrative shape criteria to glint candidates D, X, Y, and Z, GDM 820, may eliminate glints X and Z from consideration, as their respective sizes and/or shapes may be sufficiently different from the expected size and/or shape of a controlled glint to conclude that glints X and Z are not controlled glints. Glints D and Y may meet example shape criteria, however, as both may be sufficiently similar to the expected shape and/or size of a controlled glint.

After applying the shape criteria and potentially reducing the number of glint candidates, GDM 820 may implement proximity criteria in an effort to further reduce the number of glint candidates. For example GDM 820 may compare the location of each glint candidate to a hypothesis or a set of hypotheses as to where the appearing controlled glint is expected to be located. (Note that if there are only zero or one glint candidates after applying the shape criteria, the distance-based evaluation may not be performed.)

For instance, GDM 820 may determine the respective distance between the location of each glint candidate D and Y and an expected location 1032 of the appearing controlled glint. Then based on the respectively determined distance for each glint candidate, GDM 820 may determine whether or not to set the location of the glint candidate as a location for the appearing glint in the second frame 1020.

In some embodiments, the expected location 1032 may be the location of a corresponding previous hypothesis for the appearing glint candidate (e.g., the last-determined location of the appearing glint). More specifically, in an illustrative embodiment, a given hypothesis set may include an expected location for each of the glints. Accordingly, a current hypothesis set may include expected glint locations that are determined over a number of frames. As such, the expected location 1032 of an appearing glint may be set to or based on the location that was determined the previous time the glint appeared (e.g., four frames earlier. in an embodiment with four light sources).

As a specific example, consider an embodiment where each of four glints is present in three out of every frames (e.g., where there are four light sources and one is switched off during capture of each frame). In this scenario, a computing device may use the last known location of all the glints (e.g., a previous hypothesis set) to predict where each of three expected glints will appear in the next frame. The computing device can then analyze at the next video frame to estimate an eye movement that corresponds to the movement of the glints (as compared to their expected locations from the previous hypothesis set). For instance, an extended Kalman filter could be implemented in conjunction with the regression analysis that is described later herein in order to track the movement of the eye (and thus the movement of glints.

Note that it is possible that multiple glint candidates may be identified for a single appearing glint. For example, depending on the proximity criteria, it may be possible for both glint candidates D and Y to be close enough to meet the proximity criteria. If glint candidates D and Y both meet proximity criteria, then GDM 820 may output a non-ambiguous hypothesis for the location of glint D (e.g., a hypothesis set that includes two or more estimated locations for the appearing glint). In the scenario where the hypothesis for a single appearing glint is ambiguous (e.g., when there are multiple glint candidates), all of the hypotheses for the appearing glint may be discarded by GDM 820. Further, the GDM 820 may continue to rely on a previously determined location for the appearing glint. Alternatively, if there are several valid hypotheses that meet our requirements for, e.g., glint shape, geometric relationships to other glints, and/or consistency with glint locations in past frames, GDM might simply average all the valid hypotheses to determine a single hypothesis for the glint location.

In a further aspect, increasing the number of light sources (and thus the number of corresponding glints) and/or increasing the rate that the light sources are cycled on and off, may help to increase redundancy and thus reduce the number of times that multiple valid glint locations need to be resolved. In addition, if the light sources are cycled at a rate that is greater than the rate that is needed for by an gaze-tracking application, this may allow time that helps to resolve multiple valid hypotheses and/or other errors with gaze-tracking. For instance, if four LEDs are cycled on and off at 30 Hz (and captured by a 120 Hz camera, but a user interface only updates at a refresh rate of 10 Hz, GDM 820 may utilize several clock cycles between user-interface updates to resolve any problem in the hypothesis set of glint locations.

As another example, consider a scenario where gaze-tracking is implemented so as to detect eye gestures, such as rolling of the eyes, looking down or up, etc. In this scenario, it may not be necessary to detect detailed eye movements, such as might be useful for, e.g., moving a cursor on a display. As such, GDM 820 might delay for some period of time (e.g., half of a second) in order to clean up the hypothesis set of glint locations for purposes of gesture recognition. Other examples and variations on these examples are also possible.

In some embodiments, the proximity criteria may be applied to glint candidates via a greedy algorithm. More specifically, the GDM 820 may compute the distance between the location of each glint candidate and the expected location of the appearing glint (e.g., the previously determined glint location for the appearing glint). Note that if there were multiple hypotheses for location of the appearing glint the last time its location was estimated, the distance between each glint candidate in the current frame and each previous hypothesis may be determined, and the shortest distance selected to represent the distance between the glint candidate and the expected location. After determining the distance between each glint candidate and the expected location of the appearing glint, the glint candidate with the shortest distance may be set as the location for the appearing glint. Alternatively, the location or locations of all glint candidates at less than a threshold distance may be kept as part of the hypothesis set for the appearing glint.

ii. Hypothesis Set for a Disappearing Glint

In another aspect, an example method may further involve subtracting a subsequent frame from a previous frame in order to help determine a location of a disappearing glint. For example, FIG. 10D is a simplified illustration of a frame difference 1040, according to an illustrative embodiment. In particular, frame difference 1040 may be a thresholded frame difference that is determined by subtracting the second frame 1020 from the first frame 1010, and applying binary thresholding to the resulting frame difference. Thus, as shown, thresholded frame difference 1040 includes glint A, which is the disappearing glint between the first frame 1010 and the second frame 1020.

In some embodiments, the locations for a glint candidate, and the location or location(s) included in a hypothesis set for an appearing or disappearing glint, may take the form of image coordinates. That is, a location may be indicated with particular x and y coordinates in a coordinate system based on the size and shape of the frames of image data in which the glints are detected. For example, a location for a glint may be given by the x and y coordinates of a pixel that is considered to be the center point of the glint. Other examples are also possible.

In an example embodiment, GDM 820 may determine locations (or hypothesis sets of locations) for both the disappearing and appearing glint in each frame of image data. By doing so, and based on the assumption that the IR light sources will turn on and off in a known order, the GDM 820 will know which glint should appear and which glint should disappear in each frame. Accordingly, note that GDM 820 may effectively be solving two independent single-object tracking problems, rather than one multiple-object tracking problem.

Note that the examples above describe how the locations (e.g., the image coordinates) of two of the four glints can be determined using two consecutive frames (i.e., the appearing and disappearing glints). However, various aspects described herein may utilize estimated locations of all four glints (i.e., a hypothesis set for the glints). Accordingly, at a given frame, the hypothesis set may include the determined location of the appearing and/or determined location of the disappearing glint, as well as the last-determined locations of any other glints. For instance, consider a scenario where a given light source is turned off every k frames. As such, the location of the corresponding glint may be determined at frame i, then again frame i+k, and so on. As such, it may be assumed that the glint location stays at the location determined at frame i for frame i+1, to frame i+(k−1).

Alternatively, GDM 820 or another component could use an Extended Kalman filter to do prediction/re-estimation of gaze direction. In such an embodiment, GDM 820 may integrate a model of how errors in the glint detection affect the resulting gaze estimation and a model indicating reasonable eye movements (based on e.g., physical limitations of the eye), which may allow GDM 820 to balance an estimated validity of an observed glint location with a prediction of how the eye is moving at the given time.

B. Dropped-Frame Detection and Correction

In some cases, frames of image data that include glints may be dropped. This may happen for various reasons, such as an overloaded central processing unit (CPU) or a network connection (in implementations where the image data is received over a network). To make glint detection and tracking more robust and help avoid errors due to dropped frames, an example system may optionally include functionality for detecting and correcting for dropped frames.

Figure 11A:
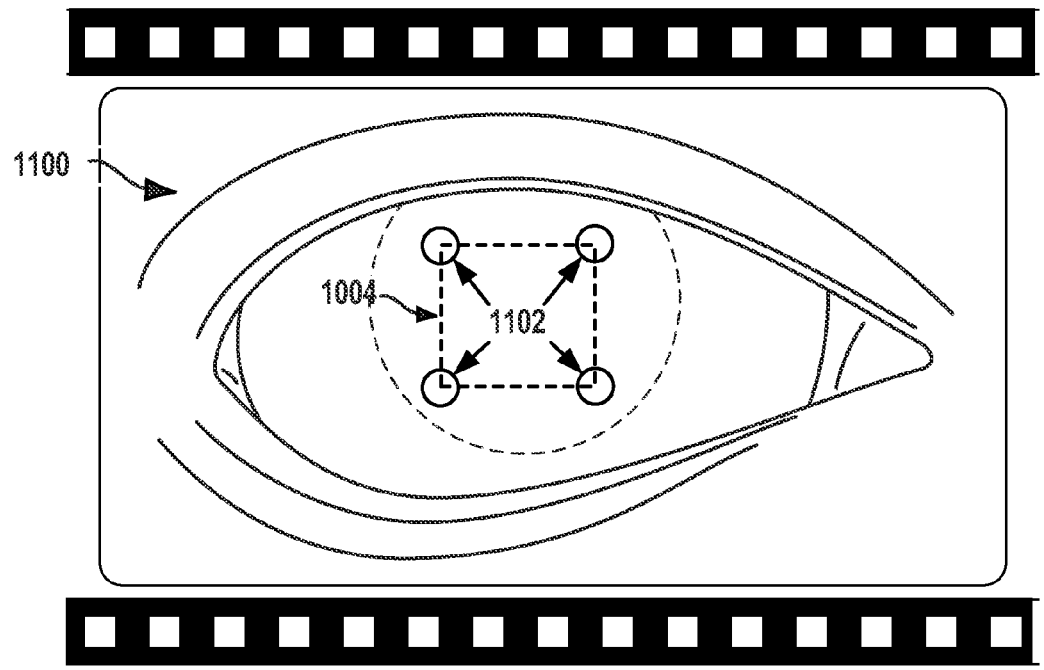
FIG. 11A shows an expected arrangement of four glints 1102 in a frame 1100, which is substantially square, according to an example embodiment.

A method for dropped-frame detection and correction will now be described by way of example, with reference to an implementation with four light sources, in which it is assumed that when all four light sources are switched on, and the shape of the four corresponding glints is approximately a square, such as is illustrated in FIG. 11A. More specifically, FIG. 11A shows an expected arrangement of four glints 1102 in a frame 1100, which is substantially square, according to an example embodiment.

Figure 11B:
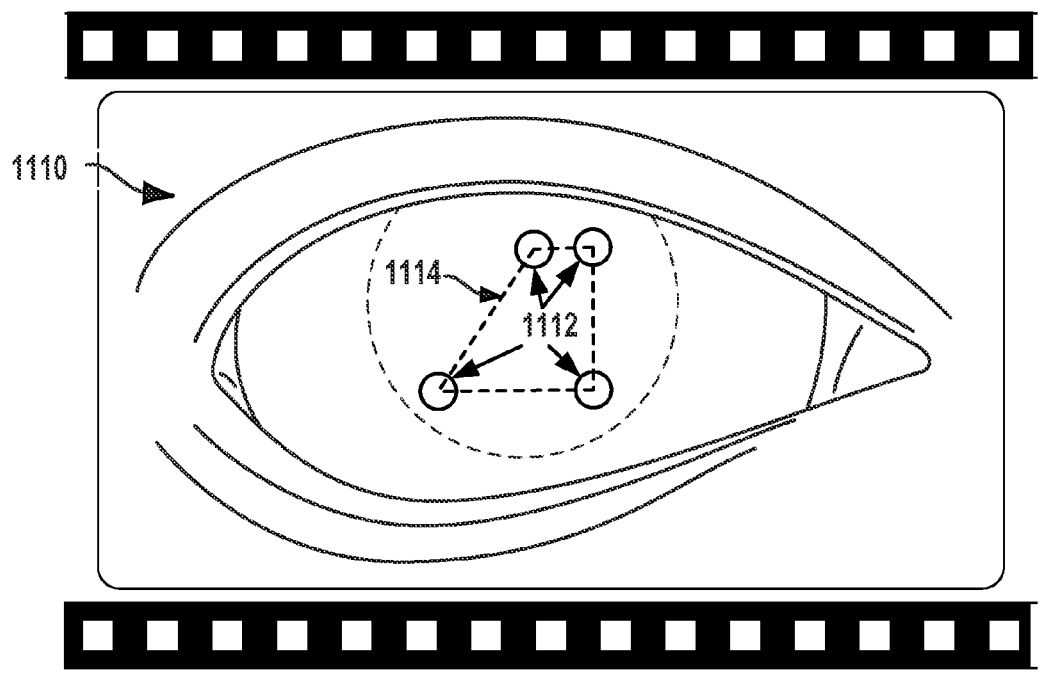
FIG. 11B shows an arrangement of four glints 1112 in a frame 1110 after a dropped frame, according to an example embodiment.

In the event that one or more frame are dropped, and the number of dropped frames is not a multiple of four, then a GDM may incorrectly identify the particular appearing and/or disappearing glint that is being looked for in the frame that is received subsequent to a dropped frame. This deviation in shape of the glint pattern due to misidentification of which glints that are switched on in a particular frame may be referred to as a glint-identification (glint-ID) shift. When glint-ID shift occurs, the shape formed by four glints may deviate from the expected square pattern. For example, FIG. 11B shows an arrangement of four glints 1112 in a frame 1110 after a dropped frame, according to an example embodiment.

To detect a dropped frame, a "squareness" value may be determined for a detected arrangement of glints. The squareness value may be based on the locations of the four glints. In particular, based on the image coordinates of the four glints 1112, the GDM may determine the perimeter P and the area A of the quadrilateral 1114 that is defined by the glints. The squareness value may then be determined as follows:

$$\text{squareness} = A * (P^2/16)$$

In this example, the denominator of 16 is set equal to the area of the square 1004. Note that this squareness value is equal to 1.0 when the four-glint quadrilateral is a square, and is smaller than 1.0 for any other quadrilateral, such as is the case for quadrilateral 1114 in FIG. 11B.

The squareness value may then be compared to a threshold. If the squareness value is less than the threshold, indicating more than a certain deviation from the expected shape defined by the glints, then the GDM 820 may conclude that a frame or frames has been dropped. In an example embodiment, the threshold may be set based on a comparison between samples of consecutive frames where it is known that no frame was dropped, and samples of consecutive frames between which it is known that a frame was dropped. The threshold may therefore be set to a value in between the squareness score for the known samples, with the exact value being selected as a matter of engineering design choice.

A calibration routine could also be used to determine the threshold for a dropped frame. For example, a calibration may be implemented where the user look at all "four corners" in their field of view, (e.g., by looking up and to the left, up and to the right, down and to the right, down and to the left) and determine the variation of the squareness. Alternatively, this process could be performed for a large sample of users, so that a reasonable (e.g., average) variation could be determined ahead of time. As yet another alternative, a physical model of the eye could be used in conjunction with computer-graphics techniques to model the expected variation, and possible squareness values that might occur if a glint position is incorrectly determined due to a dropped frame or frames.

When a dropped frame is detected, the GDM may simply output nothing or output an indication that a frame has been dropped. Further, due to glint-identification (glint-ID) shift, it may take at least 4 frames after the dropped frame for the GDM 820 to recover the square shape of the four glints, GDM 820 may correct for the shift in glints it is looking for.

In particular, the first time that a substantially square four-glint shape is detected, the GDM 820 may determine the polar coordinates of the four glints, with the center of shape defined by the four glints as the origin for the polar coordinates. Further, GDM 820 may store the polar angle vector of the four glints as reference. Then, at each subsequent frame, the polar angles may be re-determined and compared to the stored reference to find glint ID shift if any. In an example embodiment, the GDM 820 may circularly shift the newly computed polar angle vector by 0, 1, 2, and 3, and compute the similarity (L1 distance) of the shifted polar angle vector with the stored reference polar angle vector. The shift amount resulting in the highest similarity may then be used to correct for glint-ID shift.

For instance, an example how polar angles may be computed may be described in reference to FIGS. 11A and 11B. For purposes of this example, the glint 1102 in the upper right of the square 1004 may be referred to as glint 1102_A, the glint 1102 in the lower right of the square 1004 may be referred to as glint 1102_B, the glint 1102 in the lower left of the square 1004 may be referred to as glint 1102_C, and the glint 1102 in the upper left of the square 1004 may be referred to as glint 1102_D. Similarly, in FIG. 11B, the glint 1112 in the upper right of the square quadrilateral 1112 may be referred to as glint 1112_A, the glint 1112 in the lower right of the quadrilateral 1112 may be referred to as glint 1112_B, the glint 1112 in the lower left of the quadrilateral 1112 may be referred to as glint 1112_C, and the glint 1112 in the upper left of the quadrilateral 1112 may be referred to as glint 1112_D. The example computation of polar angles will now be described in greater detail.

Specifically, in FIG. 11A, a square 1004 formed by glints 1102 may have been detected. Further, the center of the square 1004 may be determined and used as a point of reference. In particular, zero degrees may be defined as being straight up from the center point, parallel to the x axis shown in FIG. 11A. As such, a GDM 820 may determine that in FIG. 11A, glint 1102_A is located at 45 degrees, glint 1102_B is located at 135 degrees, glint 1102_C is located at 225 degrees, and glint 1102_D is located at 315 degrees.

Now consider the scenario shown in FIG. 11B, and consider that frame 1100 and frame 1110 may be consecutive frames. In FIG. 11B, glints 1112 form a quadrilateral 1114, which is a substantial variation from the square 1004 formed in frame 1100. This may indicate that something has gone wrong. In particular, glints 1112_A to 1112_C are still in a similar position as their corresponding glints in the previous frame 1100 (i.e., glints 1102_A to 1102_C, respectively). However, glint 1112_D is now at approximately five degrees. Applying physical rules for eye movement, GDM 820 may determine that there is no possible movement of the eye that could result in this change in the glint pattern (e.g., from square 1004 to quadrilateral 1114. As such, it may be assumed that glint 1112_D is an ambient glint (e.g., not from one of the HMD's light sources). Or, this could result if the reflection of the same light source (e.g., the light source corresponding to glint 1102_A) is erroneously being detected twice and being fitted to both glint 1112_A and 1112_D, a scenario which is possible if a frame is dropped between frame 1100 and 1110. Accordingly, the location of glint 1112_D may be discarded. In this case, location of the glint in the upper right may be left to its previous value in the current hypothesis set, for instance, after frame 1110, the locations might be those shown by 1112_A to 1112_C and 1102D. Alternatively, the location of glint 1112_D could be adjusted or estimated based on, e.g., the movement of the other glints.

As a general matter, detection of dropped frames may utilize a model of how a glint pattern should be affected by movement of the eye, and dropped frames may then be detected when a determined location of one or more glints deviates from the model by more than a certain amount. Thus while the above examples of dropped-frame detection are based on a substantially square glint pattern, other techniques could be used to detect dropped frames based on other predefined rectangular glint patterns and possibly based on non-rectangular glint patterns as well.

C. Pupil Detection and Tracking

PDM 830 may use various techniques to detect the pupil in image data and/or to determine the location of the pupil center.

In some embodiments, PDM 830 may use a technique such as is described in R. Valenti, and T. Gevers, *Accurate Eye Center Location and Tracking Using Isophote Curvature* (CVPR 2008). Valenti describes a technique to analyze images of the eye and detect the dark circle of the pupil based on properties of the isophote curvature. According to this technique, a curvature of each image point is computed. A radius may then be estimated for a hypothesized dark circle on which the image point lies. Votes are then collected for a number of such dark circles hypotheses, and the center(s) of the circle hypothesis or hypotheses with the highest confidence score(s) may be considered as potential pupil centers.

In practice, the inventors have observed that Valenti may not function as expected when applied to digital images of the eye. For example, there may be some implementations where an alias-sensitivity issue exists. Additionally or alternatively, there may be some implementations where an inaccurate-curvedness issue exists.

Regarding the alias-sensitivity issue, the isophote curvature technique of Valenti may involve estimating the first and second order gradients of images. The estimation of the pupil center and size may be sensitive to the estimation of the gradients. Implementations of gradient estimation for digital images may be computed by convolution with a kernel, such as a Sobel kernel, which is not highly accurate, and thus may be sensitive to an alias effect.

Regarding the inaccurate-curvedness issue, Valenti describes a technique in which a curvedness value is calculated for each pixel in an image. The curvedness value is used for purposes of weighing votes in a voting process. However, because a digital image is a discrete signal rather than a continuous signal, the curvedness values are aligned with pixel boundaries, rather than to pixel centers, and may also have artifacts. As a result, the raw curvedness values may be significantly less useful for weighing votes. Accordingly, in some embodiments, PDM 830 may instead calculate the gray level for each pixel, and then use the gray level to weigh the votes.

More specifically, in some embodiments, pupil detection may involve a "balloon-blowing" technique, which grows a dark circle region from an initial point until the region hit some brighter boundary (e.g., at the edge of the pupil). To implement a balloon-blowing technique, PDM 830 may use a grayscale image of an eye as input. The PDM 830 may also determine an initial pupil-center estimate (e.g., image coordinates of a certain pixel or pixels) inside the dark pupil region of the image. The PDM may then define a small ellipse centered on the initial pupil-center estimate, and iteratively increase the size of the ellipse until the ellipse reaches the dark pupil boundary (e.g., at or near where the edge of the pupil where the iris is visible).

At each iteration in the process, PDM 830 may calculate a gray level in the image at two or more locations that correspond to the edge of the ellipse, and compare the gray levels to determine a difference between the gray levels. For example, PDM 830 may uniformly sample and compare the gray-level difference for a number of sample-point pairs, with each pair including a sample point just inside the ellipse boundary and a corresponding sample point on or just outside the ellipse boundary. PDM 830 may then adjust the size, aspect ratio, and/or rotation angle of the ellipse based on gray-level differences at the boundary of the ellipse, and repeat such adjustments iteratively until this gray-level differences are indicative of the ellipse reaching the dark pupil boundary in the image, e.g., when the inner point in the all or the majority of sample-point pairs is significantly darker than outside point (meaning the gray-scale difference is greater than a threshold difference in at least a threshold number or percentage of sample-point pairs). The center of the ellipse may then be set as the pupil center.

Note that when deciding if and/or how to adjust the ellipse, PDM 830 may compare the gray-level differences at opposite sides of the ellipse. If at least a threshold number or percentage of sample-point pairs on one side have gray-level differences above a threshold number or percentage, while those on the other side do not, this may indicate a misalignment of the ellipse (e.g., due to an inaccurate estimate of the pupil center). Accordingly, PDM may update the estimate of the pupil center, and adjust the alignment, size, and/or shape of the ellipse based on the updated estimate of the pupil center.

As a specific example, at each iteration of the balloon-blowing technique, PDM 830 may determine how many "outliers" exist (e.g., sample pairs for which the point inside the final ellipse has higher gray level and/or is brighter than the point outside the ellipse). Since an outlier may be the result of a poor fitting, the percentage of outliers in all sample points may be used as confidence score, which may be, e.g., a value between 0 and 1, with a score of 1 indicating the highest confidence in the fit to the pupil. Accordingly, the process may be repeated until the confidence score is above a predetermined threshold value.

In some embodiments, PDM 830 may first use a technique such as Valenti's isophote-curvature analysis to determine an initial estimate of the pupil center, and then apply the balloon blowing technique to help provide a more accurate estimation of the pupil center. However, it should be understood that other techniques for determining the pupil center are also possible.

In some embodiments, the isophote-curvature analysis may be used for an initial estimate of the pupil center in a first frame of image data. Subsequent frames may then use the pupil center from the previous frame as an initial estimate of the pupil center, and then apply the balloon-blowing technique described above.

For instance, to determine the pupil center at a given frame i, given a pupil center determined at a frame i−1 (e.g., the previous frame), PDM 830 may first apply the balloon blowing algorithm with the pupil center determined at frame i−1 as the initial estimate for frame i. If a confident result is obtained, then PDM 830 may compute an affinity score based on a comparison between the new pupil hypothesis and the previous one. If the affinity score is high enough, then this is considered to be a match.

As a specific example, PDM 830 may initially determine a fitting having a confidence score above a predetermined threshold, as described above, PDM 830 may then evaluate the shape affinity by e.g., comparing the size of the ellipse in the current frame i to the size of the ellipse in the previous frame i−1. An affinity score may then be determined, which is indicative of shape and/or distance affinity (e.g., how similar the shape and/or location of the ellipse in frame i is to the ellipse determined in frame i−1). In an example embodiment, a higher shape affinity score may indicate a closer match between the ellipse shapes in two frames. As such, a matching pupil shape may be considered to have been determined when the shape affinity score is above a predetermined threshold.

Other factors may also be considered when determining whether the ellipse has been correctly fitted to the pupil in a given frame. For instance, the shape of the ellipse may be compared to previous testing for the given camera (e.g., at the same focal length, eye frame, etc.) or compared to a recent history of pupil sizes, such as in the example provided above. In some embodiments, PDM 830 may consider whether the pupil center seems appropriate given the location of the pupil center in a previous frame or frames (a Kalman filter may be applied to aid in this analysis). Additionally or alternatively, PDM 830 may evaluate the eccentricity of the ellipse as compared to the eccentricity that was determined in a previous frame or frames. Further, various combinations of some or all of the above factors may be weighted in order to determine whether an ellipse has been fitted accurately enough in a given frame.

Note that in some embodiments, if there a confident estimate of the pupil center has not been determined in a previous frame i−1, or the above process to determine the pupil center in frame i fails for some other reason, then PDM 830 may start from pupil center detection to obtain a number of pupil-center candidates. Specifically, an isophote curvature algorithm may be implemented to determine a number of pupil-center candidates. Alternatively, PDM 830 may simply utilize the last location of the pupil center that was determined to be sufficiently accurate.

Other techniques for determining pupil-center candidates are also possible, such as setting the pupil center to be the darkest pixel in the image frame, assuming the image is centered on the eye (or actively centering the image on the eye) and setting the center of the image as the pupil center, or making an even grid of pupil center candidates across an image of the eye. In any such case, PDM 830 may then apply the balloon-blowing technique a number of times, starting from each of the pupil-center candidates, and select the pupil-center candidate with highest balloon-blowing score as the pupil center at the current frame. Alternatively, some or all of such techniques could be used to obtain multiple pupil-center candidates, and PDM 830 could then select the candidate that best matches the size, shape, and location for an average pupil (e.g., based on a model of the eye).

D. Feature Normalization

In embodiments, one or more of the systems described herein may be used to detect and track glints and/or pupil locations. The accuracy at which the pupil locations in an image is mapped to a gaze location on a display may be based at least in part on the location of the system and/or device used in the system relative to the user's eye. For example, when a device remains in the same location relative to the user's eye, the mapping of the pupil location to the gaze location on a display may be invariant. However, when the device drifts or otherwise changes location in relation the user's eye, the mapping of the pupil location to the gaze location on the display may vary. In embodiments, tolerance to the device drift may be obtained by normalizing the pupil locations with glint locations. The normalization method may be based on the number of glints from the detection and tracking systems.

In embodiments where a single glint is received from the detection and tracking systems, the single glint may be normalized using a translation normalization. The feature normalization module 840, for example, may perform the translation normalization by computing a relative vector from the pupil location to the glint location. This normalization method may provide invariance to the pupil translation in image space.

Figure 12B:
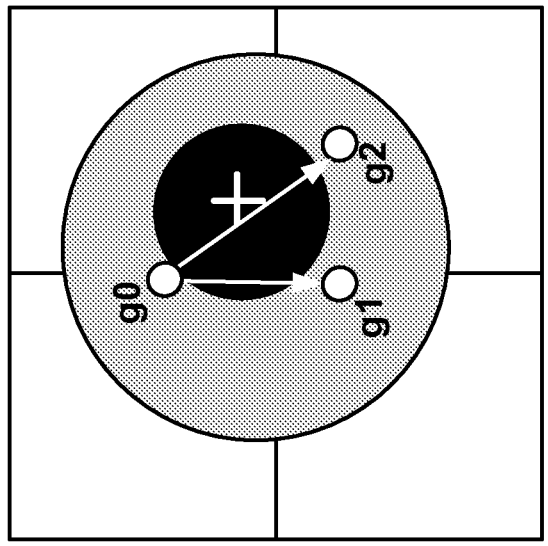
FIG. 12B is a simplified illustration of affinity normalization with three glints, according to an exemplary embodiment.
Figure 12A:
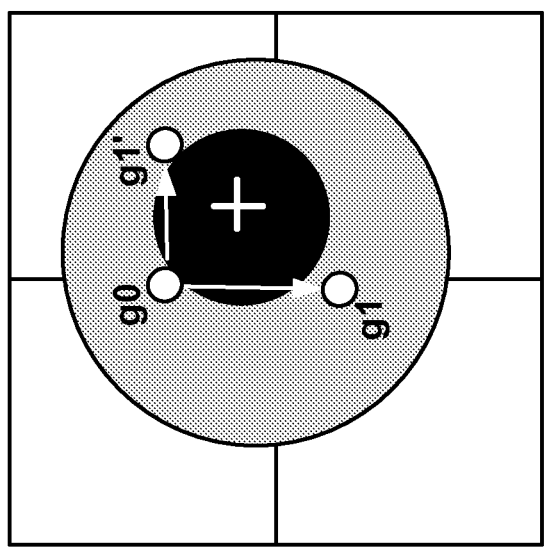
FIG. 12A is a simplified illustration of a similarity normalization with two glints, according to an exemplary embodiment.

FIG. 12A is a simplified illustration of a similarity normalization with two glints, according to an exemplary embodiment. In particular, FIG. 12A includes a first glint g0, a second glint g1, and a calculated glint g1', which may be calculated based on the locations of the first glint g0 and the second glint g1. FIG. 12A also includes a first vector g0-g1 and a second vector g0-g1' that may be determined based on the locations of the first glint g0, the second glint g1, and/or the calculated glint g1'. The second vector g0-g1' may be perpendicular to the first vector g0-g1 and may be used to form a coordinate framework with the first vector g0-g1. The feature normalization module 840 may utilize similarity normalization to compute a normalized pupil location using the created coordinate framework. In embodiments, the normalized pupil location may be invariant to scaling, rotation, and/or translation in image space.

FIG. 12B is a simplified illustration of affinity normalization with three glints, according to an exemplary embodiment. In particular, FIG. 12B includes a first glint g0, a second glint g1, and a third glint g2. FIG. 12B also includes a first vector g0-g1 and a second vector g0-g2. The first vector g0-g1 and the second vector g0-g2 may be used to form a coordinate framework. In embodiments, the feature normalization module 840 may utilize affinity normalization to compute a normalized pupil location using the created coordinate framework. In embodiments, the normalization process may bring invariance to the affine transformation of the pupil location in image space.

In embodiments where four glints are available, the system or device in the system may utilize homography normalization to normalize the pupil location. In particular, a device may compute a homography from the four glints to a unit square (i.e., $[0, 1] \times [1, 0]$). The homography may be applied to the pupil location to obtain the normalized pupil location. This homography normalization may provide invariance to perspective transformation of the pupil location in image space.

While the normalization methods have been described above in reference to one, two, three, or four glints, it should be understood that additional glints may also be used for purposes of normalizing the pupil location. The normalization methods used when there are in excess of four glints may include one or more algorithms known to those of skill in the art. In some examples, normalizing additional glints may result in additional invariance of the pupil location in image space. However, additional glints may also result in additional noise, which may increase the gaze estimation error and result in the calibration and/or gaze estimation module having to do additional low pass filtering to the observations to reduce negative effects from noises.

E. Calibration

Figure 13:
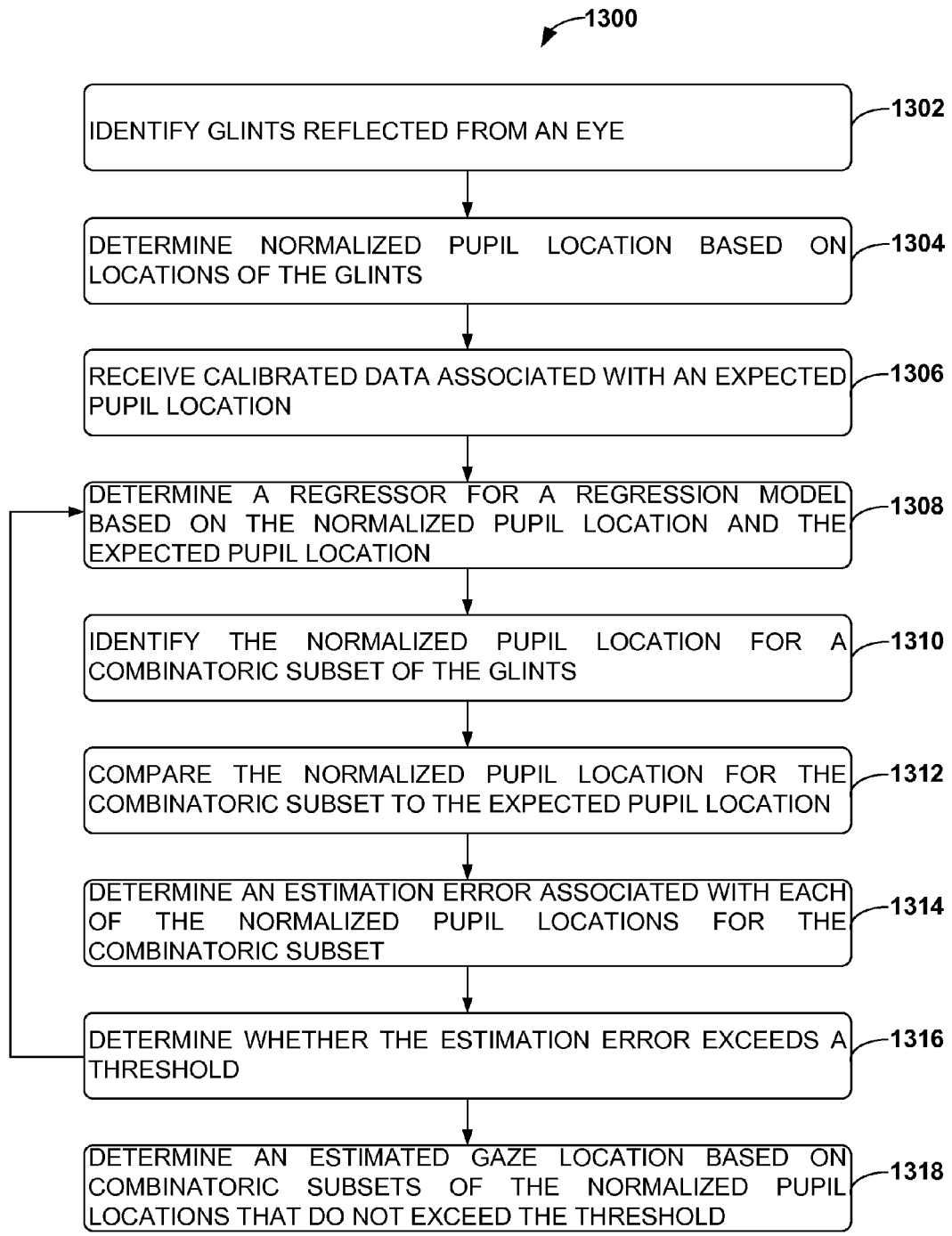
FIG. 13 is a flow chart illustrating a method 1300, according to an exemplary embodiment.

FIG. 13 is a flow chart illustrating a method 1300, according to an exemplary embodiment. Method 1300 shown in FIG. 13 presents an embodiment of a method that could be used and/or be performed by a device or components of the device. An example device may include the wearable computing system illustrated in FIGS. 1A-1D or any number of other devices associated with the system. Method 1300 may include one or more operations, functions, or actions as illustrated by one or more of blocks of method 1300. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 1300 and other processes and methods disclosed herein, the flowchart shows functionality and operation of one possible implementation of the present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include a non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage system. The computer readable medium may, for example, be considered a computer readable storage medium or a tangible storage device.

In addition, for the method 1300 and other processes and methods disclosed herein, each block in FIG. 13 may represent circuitry that may be wired to perform the specific logical functions in the process.

At block 1302, the method 1300 may involve identifying glints reflected from an eye. A glint may include a reflection of an infrared light on a corneal surface of a user's eye. The infrared light may be presented to the user in a clockwise or counterclockwise manner. The glints may be identified using any number of devices, such as the wearable computing system. As described herein, the number of glints may range up to four glints; however, additional embodiments may include more than four glints.

At block 1304, the method 1300 includes determine normalized pupil location based on locations of the glints. The normalized pupil location may be determined by a device, such as the wearable computing system. As discussed in more detail herein, the normalization process may include receiving the identified glints, which may be positioned to form a square. The type of normalization performed on the glints may vary based on the number of glints that are received. Thus, for example, when a single glint is identified and received, the method 1300 may determine a relative vector from a pupil location to the location of one of the glints using translation normalization. When two glints are identified and received, a coordinate framework with the two glints may be identified, and a pupil location on the coordinate framework may be determined using a similarity normalization of the two glints. Similarly, when three glints are identified and received, a coordinate framework with the three glints may be identified, and a pupil location on the coordinate framework may be determined using an affinity normalization of the three glints. Likewise, when four glints are identified and received, a coordinate framework with the four glints may be identified, and a pupil location on the coordinate framework may be determined using an homography normalization of the four glints.

At block 1306, the method 1300 includes receive calibrated data associated with an expected pupil location. Calibrated data may generally include data that is used for purposes of calibration. An example of calibrated data may include expected pupil location data, which may represent a location on a Cartesian plane that may be shown to a user. The user may be asked to fixate or otherwise focus on the expected pupil location, and information associated with the user's gaze may be used by the device to identify glints reflected from the user's eye. In yet further embodiments, the expected pupil location may be a default or previously calculated location.

At block 1308, the method 1300 includes determine a regressor for a regression model based on the normalized pupil location and the expected pupil location. This process may be performed by a device, such as the wearable computing system. In embodiments, one or more of the determined regressors may be used for calibration purposes.

More specifically, the process of mapping a normalized pupil location in an image to a gaze location on a display is a non-linear function. This is in part because the retina surface is not on a plane, and the IR camera that may be obtaining gaze data may be very close to the eye. Due to the non-linear nature of the function, a polynomial regression may be used for calibration purposes. The polynomial regression model may be learned for x coordinates and/or y coordinates on the Cartesian plane or other coordinate framework. In embodiments, not all of the coefficients in the polynomial regression may be necessary. An exemplary polynomial regression with an order of three may be represented as: gaze $x|y=a0+a1*x+a2*y+a3*x^2+a4*y^2+a5*xy+a6*x^2y+a7*xy^2$. While calibration using a polynomial regression is used for descriptive purposes, it should be understood that other algorithms may be used for purposes of calibration. For example, artificial neural networks may be an alternative calibration method. Exemplary artificial neural network may require a higher accuracy and a lower risk of overfitting relative to the polynomial regression.

Determining a regressor may be an iterative process, which may broadly include blocks 1310, 1312, 1314, and/or 1316, for example. In particular, at block 1310, the method 1300 includes identify the normalized pupil location for a combinatoric subset of the glints. This process may be performed by a device, such as the wearable computing system, and may include the identification of a number of identified glints. Based on the number of identified glints, the wearable computing system may determine the total number of combinations of the identified glints using the combinatorics equation C(n, r), where n may represent the number of available glints and r may represent the number of glints chosen from the number of available glints, for example. Each of the combinatoric subsets of the glints may be normalized based on the number of glints in the combinatoric subset. Thus, for example, when n=4 glints and r=2 glints, the number of combinatoric subsets may be six. Each of the six combinatoric subsets may be normalized using a similarity normalization, for example.

At block 1312, the method 1300 includes compare the normalized pupil location for the combinatoric subset to the expected pupil location. This process may be performed by a device, such as the wearable computing system. In embodiments, the process of comparing the normalized pupil location of the combinatoric subset to the expected pupil location may be used to determine a distance, a relative position, etc., of the normalized pupil location of the combinatoric subset to the expected pupil location.

At block 1314, the method 1300 includes determine an estimation error associated with each of the normalized pupil locations for the combinatoric subset. This process may be performed by a device, such as the wearable computing system. In some examples, this process may include a determination of an estimation error. The estimation error may be based on a maximum allowable estimation error for the system, based on historical estimation errors, based on a predefined estimation error, etc. In embodiments, the estimation error may be specific to each regressor associated with the normalized pupil location. In yet further embodiments, however, the estimation may be associated with a combination of multiple regressors associated with the normalized pupil location.

At block 1316, the method 1300 includes determine whether the estimation error exceeds a threshold. This process may be performed by a device, such as the wearable computing system. In embodiments, the threshold may be a predefined level, number of regressors, and/or a percentage. Moreover, in some embodiments, the threshold may be based on the system, the gaze data, or any number of alternative variables. The process of determining whether the estimation error exceeds a threshold may be performed by comparing the estimation error associated with each individual regressor to the threshold. Optionally and/or additionally, the determination may be performed by comparing the estimation error associated with a plurality of regressors, which have been combined in one way or another, to the threshold. Thus, for example, an average estimation error may be determined for one or more of the regressors and compared to the threshold. Likewise, in another example, a maximum estimation error may be determined for one or more of the regressors and compared to the threshold. In yet another example, a predefined number of the regressors with the highest estimation error may be identified and determined to exceed the threshold.

In those examples where the estimation error exceeds the threshold, the regressors associated with the excessive estimation error(s) may be excluded from use in determining the regression model. This process may continue until all of the combinatoric subsets of the glints for a normalized pupil location have been identified, compared to the expected pupil location, and associated with an estimation error, which may or may not exceed the threshold.

In some examples, the device may determine the number of regressors that do not exceed the threshold and further determine whether the number of regressors that do not exceed the threshold are enough to train the regression model. If not, the device may receive additional data as described in reference to block 1302, for example, and continue through the steps of the method 1300 until enough training data that is within the threshold is available.

At block 1318, the method 1300 includes determine an estimated gaze location based on combinatoric subsets of the normalized pupil locations that do not exceed the threshold. This process may be performed by a device, such as the wearable computing system. In some examples, the estimated gaze location may be determined by taking a median or mean of the normalized pupil locations for each of the combinatoric subsets of the normalized pupil locations. Moreover, once enough training data exists, the device may use the ensemble of training data to identify one or more regressors for the regression model.

In some embodiments, the training data that is within the threshold may be stored in a database. Thus, for example, training data associated with a user may be stored in a user profile and used for calibration purposes when the user interacts with the device, or any other device communicatively coupled to the device. Moreover, in further examples, the training data may be associated with a default profile, a generic user profile, etc. In such examples, the training data may be aggregated and used as a default calibration.

In embodiments, the normalization and calibration processes of method 1300 may provide some tolerance to the wearable computing system or other device relative to the eye. For example, the gaze tracker may be robust enough to provide consistent calibrations when the device moves away from or closer to the eye along a visual axis, when the device rotates along a visual axis, when the device moves along a circular orbit trajectory centered by the fovea, etc. In those embodiments where the gaze tracker lacks adequate robustness, such as when the IR camera is moved freely, shifted vertically along a nose bridge, etc., an additional calibration process may be used to learn a camera drift. In some examples, the camera drift may be approximated by a linear offset at the gaze space. Thus, for example, the offset at the gaze space may be for coefficient a0 in the above determined polynomial regression. The process of identifying the offset may be performed using one or more of the calibration points.

Figure 14:
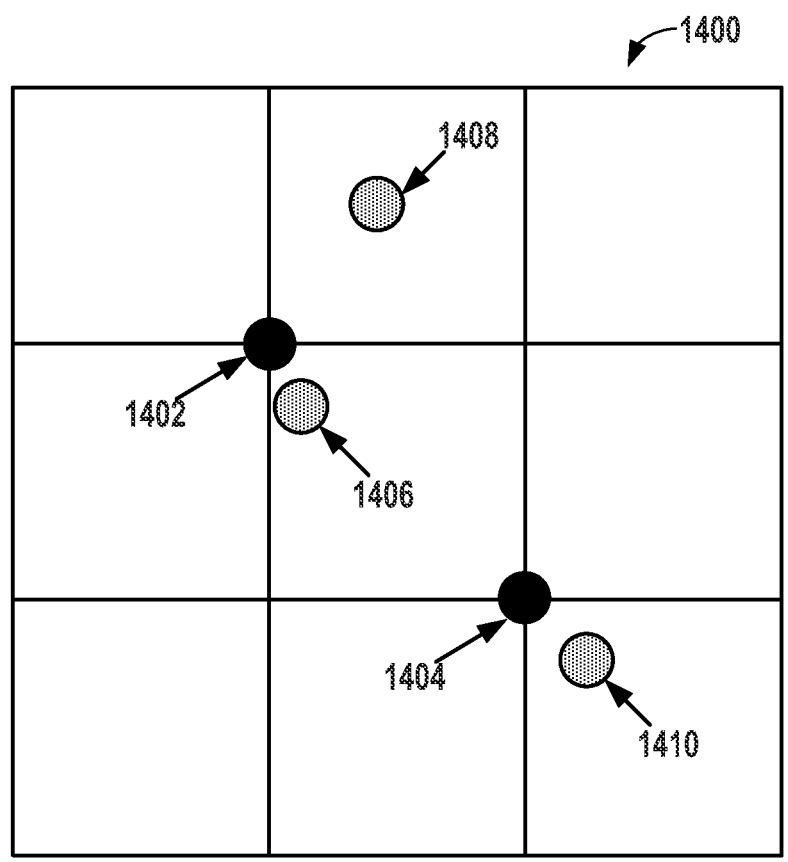
FIG. 14 is a simplified illustration of a calibration grid, according to an exemplary embodiment.

FIG. 14 illustrates a simplified illustration of calibration data, according to an exemplary embodiment. In particular, FIG. 14 illustrates a Cartesian coordinate plane 1400 having at least one expected gaze location 1402, 1404 and at least one normalized pupil location 1406, 1408, and 1410. The Cartesian coordinate plane 1400 may be presented to a user via a device, such as the wearable computing system illustrated in FIGS. 1A-1D. In embodiments, the Cartesian coordinate plane 1400 may be presented with or without gridlines. While the expected gaze location 1402, 1404 and the normalized pupil location 1406, 1408, and 1410 are represented as points on the Cartesian coordinate plane 1400, it should be understood that any number of visual displays may be used to represent the expected gaze location 1402, 1404 and/or the normalized pupil location 1406, 1408, and 1410.

The expected gaze location 1402, 1404 may be presented to a user and represent a location that the user is expected to gaze at during a calibration process. As described in reference to FIG. 13, the calibration process may include presenting the expected gaze location 1402, 1404 to a user. The user may gaze at the expected gaze location 1402, 1404 and the user's gaze, or data associated therewith, may be obtained and/or recorded using any number of possible input devices. An example input device may include an IR camera, which may or may not be releasably attached to the wearable computing system. The data obtained by the input device may be analyzed by the system. In embodiments, this analysis may include the identification of one or more glints. One or more of the glints may be normalized, as discussed elsewhere herein, and used to identify a location of the user's pupil. This location may represent a normalized pupil location 1406, 1408, and 1410.

In embodiments, multiple normalized pupil locations 1406, 1408, and 1410 may be received and/or identified by the system. For example, the system may present a first expected gaze location 1402 to the user. In response, the system may receive and/or identify a first normalized pupil location 1406 associated with the first expected gaze location 1402. After presenting the first expected gaze location 1402 to the user, the system may present a second expected gaze location 1404 to the user and receive and/or identify a second normalized pupil location 1410 associated with the second expected gaze location 1404. In embodiments, the system may present the first expected gaze location 1402 (and/or any other expected gaze location) to the user multiple times and receive additional gaze locations, such as third gaze location 1408. This process may continue until a predetermined number of expected gaze locations 1402, 1404 have been presented to the user, until a predetermined number of normalized pupil locations 1406, 1408, 1410 have been received and/or identified, for a predetermined period of time, etc.

In embodiments, the calibration process may include presenting the expected gaze location 1402, 1404 to the user one at a time. In embodiments, the expected gaze location 1402 that was presented to the user, as well as all or part of the received and/or identified normalized pupil locations 1406, 1408 associated with the presented expected gaze location 1402, may be used as inputs to train a regression model. The number of inputs may be analyzed to determine if there exist enough inputs to train the regression model. The number of inputs that may be needed to train the regression model may be based in whole or in part on a degree of accuracy required for the model, an amount of time available to collect and/or receive inputs, a predetermined number of inputs, etc. If enough inputs do not exist, the expected gaze location 1402 may be presented to the user to collect additional inputs. If enough inputs do exist, the inputs may be analyzed to determine whether any outliers exist. An outlier may exist when an input falls outside of the three sigma rule. If an outlier exists, the outlier may be removed. Thus for example, the third normalized pupil location 1408 may be an outlier and removed because the third normalized pupil location 1408 falls outside of a predetermined range, which may be predefined and/or otherwise determined by the system, for example. After removing one or more outliers, the system may determine if enough inputs remain to train the regression model. If not, additional inputs may be obtained and analyzed to determine if the additional inputs are outliers.

Once enough inputs that are not outliers have been received, the system may use the inputs to train the regression model. As described in reference to FIG. 13, the training process may include training multiple regressors or independent variables using different subsets of the glints for normalization. Thus, if the first normalized pupil location 1406 includes four glints, all four of the glints may be normalized using a homography normalization and used to train the regression model. A subset of the four glints associated with the first normalized pupil location 1406 may also be identified and used to further train the regression model. As an example, if the four glints include glints 0, 1, 2, and 3, then a subset of the four glints including glints 0, 1, and 2 may be normalized using an affine transformation and used to further train the regression model. In another example, of the four glints, glints 0, 1, and 3 may be normalized using an affine transformation and used to train the regression model. Similarly, glints 1, 2, and 3 and/or glints 0, 1, and 3 may be normalized using an affine transformation and used to train the regression model. This iterative process may continue using a similarity normalization of two of the four glints, and a translation normalization of each of the four glints independently. In this way, there may be a single regressor utilizing four glints, four regressors utilizing three glints, six regressors utilizing two glints, and four regressors utilizing a single glint for a total of 15 regressors associated with the normalized pupil location 1406. The number of combinations (and the corresponding number of possible regressors associated with each normalized pupil location 1406, 1408, and 1410) may be calculated using the combinatorics equation C(n, r) where n may represent the number of available glints for a normalized pupil location 1406, 1408, and 1410 and r may represent the number of glints chosen from the number of available glints, for example.

Once the regressors for the first normalized pupil location 1406 have been determined, an estimation error for one or more of the regressors relative to the expected gaze location 1402 may be determined and compared to a threshold. Thus, for example, an average estimation error, a maximum estimation, or other estimation error may be compared to a threshold, which may be predefined and/or otherwise determined by the system. Those regressors that exceed or are otherwise outside of the threshold may be disabled. Moreover, in some examples, a predetermined number of the regressors having the highest estimation errors may be disabled (e.g., not used by the system). If the average estimation error for the multiple regressors for the first normalized pupil location 1406 exceeds the threshold, the expected gaze location 1402 may be reshown to the user and the system may collect new data, such as a new normalized pupil location associated with one or more glints. New regressors based on the new normalized pupil location may be identified and an estimation error associated with the new normalized pupil location may be compared to a threshold in a manner similar to that described above. This iterative process may continue until a predetermined number or percentage of regressors that fall within the threshold have been identified for the expected gaze location 1402. Once the predetermined number or percentage of regressors have been obtained, the system may determine a regressor for the regression model based on one or more of the average locations, median locations, etc. of the first normalized pupil location 1406 compared to the expected gaze location 1402 for purposes of calibration.

F. Gaze Estimation and Tracking

A gaze may be estimated using the regressors from the calibration process. In particular, gaze estimation may be determined by combining one or more of the multiple regressors and/or estimations of the multiple regressors. The method of combining the multiple regressors may vary in embodiments and include, for example, a majority voting style method of combining the multiple regressors.

As an example, if k glints are tracked in a first frame, then all of the valid gaze regressors that use a subset of the k detected glints for pupil location normalization may be used to estimate the gaze. Thus, if glints 0 and 1 are tracked, then the one glint regressors using glint 0 and glint 1, respectively, as well as the two glint regressors using glint 0 and glint 1 may be used to estimate the gaze. In embodiments, the median x and/or y coordinates of the active regressors' estimation results may be taken as the gaze location of the frame. In further embodiments, a median filtering may be applied on a temporal dimension such that the median x and/or y coordinates of the gaze locations in the past n frames may be taken as the current gaze location.

Subsequent to the calibration and/or gaze estimation process, the user may be presented with a validation animation to allow the user to verify the gaze estimation. In some examples, the validation animation may include a grid as a background and a visual representation of the estimated gaze location (e.g., via a dot on the grid). In this manner, the user may view the estimated gaze location. In embodiments, the user may confirm or deny the estimated gaze location based on the validation animation.

While a number of possible gaze estimation techniques have been described herein, it should be understood that described techniques are non-limiting. Moreover, all of the techniques need not be applied to determine an estimated gaze location. For example, in some embodiments, the gaze estimation may be determined without the calibration process. Moreover, in yet further embodiments, the gaze estimation may be determined using a different method of combining the multiple regressors, for example.

VI. CONCLUSION

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying figures be interpreted as illustrative and not in a limiting sense.

What is claimed is:

1. A method comprising:
   receiving glint-location data indicating a location for each of one or more glints that are reflected from an eye, wherein the glint-location data is captured by an imaging device that is associated with a head-mountable display (HMD);
   determining a plurality of normalized pupil locations comprising at least a first and a second normalized pupil location, wherein each normalized pupil location is determined based on the glint-location data for a different combinatoric subset of the one or more glints;
   determining a regression model to fit the plurality of normalized pupil locations to an expected gaze location; and
   performing, by a computing device, a gaze-tracking process based on the regression model.

2. The method of claim 1, wherein the one or more glints include reflections of an infrared light on a corneal surface.

3. The method of claim 2, further comprising providing the infrared light in a clockwise manner.

4. The method of claim 2, further comprising providing the infrared light in a counterclockwise manner.

5. The method of claim 1, wherein the glint-location data includes location data for four glints that are positioned to form a square.

6. The method of claim 1, wherein determining the plurality of normalized pupil locations further comprises:
   determining a relative vector from the first normalized pupil location to the glint-location data using a translation normalization.

7. The method of claim 1, wherein determining the plurality of normalized pupil locations further comprises:
   determining a coordinate framework with two glints from the one or more glints; and
   determining the first normalized pupil location on the coordinate framework using a similarity normalization of the two glints.

8. The method of claim 1, wherein determining the plurality of normalized pupil locations further comprises:
   determining a coordinate framework with three glints from the one or more glints; and
   determining the first normalized pupil location on the coordinate framework using an affinity normalization of the three glints.

9. The method of claim 1, wherein determining the plurality of normalized pupil locations further comprises:
   determining a coordinate framework with four glints from the one or more glints; and
   determining the first normalized pupil location on the coordinate framework using a homography normalization of the four glints.

10. The method of claim 1, wherein the regression model is a polynomial regression model.

11. A system comprising:
    at least one processor;
    a non-transitory computer-readable medium; and
    program instructions stored on the non-transitory computer-readable medium and executable by the at least one processor to cause the system to:
    receive glint-location data indicating a location for each of one or more glints that are reflected from an eye, wherein the glint-location data is captured by an imaging device that is associated with a head-mountable display (HMD);
    determine a plurality of normalized pupil locations comprising at least a first and a second normalized pupil location, wherein each normalized pupil location is determined based on the glint-location data for a different combinatoric subset of the one or more glints;
    determine a regression model to fit the plurality of normalized pupil locations to an expected gaze location; and
    perform a gaze-tracking process based on the regression model.

12. The system of claim 11, further comprising program instructions stored on the non-transitory computer-readable medium and executable by the at least one processor to cause the system to:
    determine an estimation error associated with at least the first and the second normalized pupil location; and
    determine the estimated gaze location by taking a median of at least the first and the second normalized pupil locations having the estimation error less than a threshold.

13. The system of claim 12, wherein determining the estimation error further comprises:
    determining an average estimation error associated the first normalized pupil location;
    comparing the average estimation error to a threshold; and
    eliminating the first normalized pupil location when the average estimation error exceeds the threshold.

14. The system of claim 12, wherein determining the estimation error further comprises:
    determining a maximum estimation error associated with the first normalized pupil location;
    comparing the maximum estimation error to a threshold; and
    eliminating the first normalized pupil location when the maximum estimation error exceeds the threshold.

15. A non-transitory computer-readable medium having stored thereon instructions executable by a computing device having at least one processor to cause the computing device to perform functions comprising:
    receiving glint-location data indicating a location for each of one or more glints that are reflected from an eye, wherein the glint-location data is captured by an imaging device that is attached to a head-mountable display (HMD);
    determining a plurality of normalized pupil locations comprising at least a first and a second normalized pupil location, wherein each normalized pupil location is determined based on the glint-location data for a different combinatoric subset of the one or more glints;

determining a regression model to fit the plurality of normalized pupil locations to an expected gaze location; and performing, by a computing device, a gaze-tracking process based on the regression model.

16. The non-transitory computer readable medium of claim 15, wherein the regression model is a polynomial regression model.

17. The non-transitory computer readable medium of claim 15, wherein the glint-location data includes location data for four glints.

18. The non-transitory computer readable medium of claim 15, wherein the instructions are further executable by the computing device to cause the computing device to perform functions comprising:
   determining an average estimation error associated with the second normalized pupil location;
   comparing the average estimation error to a threshold; and
   eliminating the second normalized pupil location when the average estimation error associated with the second normalized pupil location exceeds the threshold.

19. The non-transitory computer readable medium of claim 15, wherein the instructions are further executable by the computing device to cause the computing device to perform functions comprising:
   determining an estimation error associated with at least the first and the second normalized pupil location; and
   determining the estimated gaze location by taking a median of at least the first and the second normalized pupil locations having the estimation error less than a threshold.

20. The non-transitory computer readable medium of claim 19, wherein the instructions are further executable by the computing device to cause the computing device to perform functions comprising:
   determining an average estimation error associated the first normalized pupil location;
   comparing the average estimation error to a threshold; and
   eliminating the first normalized pupil location when the average estimation error exceeds the threshold.

* * * * *